United States Patent
Chang et al.

(10) Patent No.: US 8,557,549 B2
(45) Date of Patent: Oct. 15, 2013

(54) MICROORGANISM PRODUCING O-PHOSPHOSERINE AND METHOD OF PRODUCING L-CYSTEINE OR DERIVATIVES THEREOF FROM O-PHOSPHOSERINE USING THE SAME

(75) Inventors: Jin Sook Chang, Seoul (KR); Jae Hyun Jo, Seoul (KR); Hyun Ae Bae, Incheon (KR); Byeong Cheol Song, Uiwang-si (KR); Sol Kim, Seoul (KR); Hye Won Kim, Seongnam-si (KR)

(73) Assignee: CJ Cheildjedang Corporation, Seoul (KR)

( * ) Notice: Subject to any disclaimer, the term of this patent is extended or adjusted under 35 U.S.C. 154(b) by 0 days.

(21) Appl. No.: 13/278,105

(22) Filed: Oct. 20, 2011

(65) Prior Publication Data

US 2012/0190082 A1    Jul. 26, 2012

(30) Foreign Application Priority Data

Oct. 20, 2010  (KR) ...................... 10-2010-0102664
Aug. 26, 2011  (KR) ...................... 10-2011-0086081

(51) Int. Cl.
*C12P 13/12*    (2006.01)

(52) U.S. Cl.
USPC .......................................................... 435/113

(58) Field of Classification Search
USPC .......................................................... 435/113
See application file for complete search history.

(56) References Cited

PUBLICATIONS

Westrop et al., JBC, 281(35), 25062-25075, 2006.*

* cited by examiner

*Primary Examiner* — Maryam Monshipouri
(74) *Attorney, Agent, or Firm* — Cooley LLP

(57) ABSTRACT

The present invention provides methods for the production of cysteine or derivates thereof by culturing a microorganism having reduced activity of endogenous phosphoserine phosphatase and enhanced activity of phosphoglycerate dehydrogenase and/or phosphoserine aminotransferase. The O-phosphoserine produced by such an organism can then be reacted with a sulfide in the presence of a sulfydrylase or a microorganism expressing a sulfhydrylase to produce cysteine or a derivative thereof. Microorganisms having the properties noted above are also provided herein.

17 Claims, 5 Drawing Sheets ically by acid hydrolysis of human hairs or animal feathers (Biotechnology of the Amino Acids Production edited by Ko Aida, p 217-223, 1986). However, not only does the production of cysteine from hairs or feathers ensure a yield of as low as 7~8%, but also the use of hydrochloric acid or sulfuric acid produces a lot of waste resulting in environmental pollution. Further, extraction from hairs or feathers may induce the user to have a strong adversion thereto. These problems have caused a push for the development of environmentally friendly production processes of L-cysteine. The main contemporary route involves fermentation utilizing microorganisms.

MICROORGANISM PRODUCING O-PHOSPHOSERINE AND METHOD OF PRODUCING L-CYSTEINE OR DERIVATIVES THEREOF FROM O-PHOSPHOSERINE USING THE SAME

CROSS-REFERENCE TO RELATED APPLICATIONS

This application claims the priority benefit of Korean Patent Application Nos. 10-2011-0086081, filed Aug. 26, 2011 and 10-2010-0102664, filed Oct. 20, 2010. The contents of these patent applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_004_01US_ST25.txt. The text file is 64 KB, was created on Oct. 20, 2011, and is being submitted electronically via EFS-Web.

TECHNICAL FIELD

The present invention relates to a method for production of cysteine or its derivatives using O-phosphoserine as an intermediate and recombinant microorganism for use in production of O-phosphoserine.

BACKGROUND ART

L-cysteine is an amino acid that plays an important role in sulfur metabolism of all living organisms. It is used in the biosynthesis of proteins, such as hair keratin, glutathione, biotin, methionine and other sulfur-containing metabolites as well as serving as a precursor of coenzyme A. In addition, the biosynthesis of cysteine is known to be closely associated with the biosynthesis of other amino acids including L-serine, L-glycine, and L-methionine. Industrially, L-cysteine and its derivatives find applications in a variety of fields including the pharmaceutical industry (for treatment of bronchial diseases), the cosmetics industry (in hair shampoo, compositions for permanent waves), and the food industry (antioxidants, flavorant enhancers, dough aids, etc.).

L-cysteine was once obtained industrially by acid hydrolysis of human hairs or animal feathers (Biotechnology of the Amino Acids Production edited by Ko Aida, p 217-223, 1986). However, not only does the production of cysteine from hairs or feathers ensure a yield of as low as 7~8%, but also the use of hydrochloric acid or sulfuric acid produces a lot of waste resulting in environmental pollution. Further, extraction from hairs or feathers may induce the user to have a strong adversion thereto. These problems have caused a push for the development of environmentally friendly production processes of L-cysteine. The main contemporary route involves fermentation utilizing microorganisms.

Representative among the microbial production of L-cysteine is 1) the biological conversion of D,L-ATC using a microorganism (Ryu O H, Ju J Y and Shin C S, Process Biochem., 32:201-209, 1997). This conversion process is, however, difficult to apply industrially due to the low solubility of the precursor D,L-ATC. 2) Another method of L-cysteine production is direct fermentation using *E. coli* (Patent No. EP0885962B; Wada M and Takagi H, Appl. Microbiol. Biochem., 73:48-54, 2006). Excessive accumulation of L-cysteine within microorganisms incurs intracellular toxicity, exhibiting a limitation in the production of L-cysteine at a high concentration. To overcome this drawback, L-cysteine-exporting proteins are employed, but there have been no significant improvements in productivity.

Referring to the biosynthesis pathway of L-cysteine in microorganisms and plants, O-acetyl-serine (OAS) acts as an intermediate precursor providing the carbon backbone of L-cysteine (Kredich N M and Tomkins G M, J. Biol. Chem., 241: 4955-4965, 1966). The enzyme O-acetylserine sulfhydrylase (OASS), using hydrogen sulfide as a sulfur donor, catalyses the conversion of O-acetylserine to cysteine. Alternatively, $SO_4$ may be reduced to thiosulfate for use as a sulfur donor in cysteine production (Nakamura T, Kon Y, Iwahashi H and Eguchi Y, J. Bacteriol., 156: 656-662, 1983). Therefore, cystein may be produced using microorganisms accumulating OAS and OASS using various sulfur donors (U.S. Pat. No. 6,579,705). The cysteine biosynthesis pathway via OAS uses the two enzymes of serine acetyltransferase (CysE), which catalyzes the conversion of OAS from serine, and cysteine synthase (CysK), which catalyzes the conversion of OAS to cysteine. Among them, serine acetyltransferase (CysE) is highly sensitive to feedback inhibition by the final product cysteine (Wada M and Takagi H, Appl. Microbiol. Biochem., 73:48-54, 2006).

DISCLOSURE

Technical Problem

Leading to the present invention, the present inventors found out the existence of O-phosphoserine sulfhydrylase (OPSS) in *Aeropyrum pernix, Mycobacterium tuberculosis,* and *Trichomonas vaginalis* that takes an O-phospho-L-serine (OPS)-specific pathway, rather than the OAS-specific pathway, to synthesize L-cysteine through intensive research (Mino K and Ishikawa K, FEBS letters, 551: 133-138, 2003; Burns K E, Baumgart S, Dorrestein P C, Zhai H, McLafferty F W and Begley T P, J. Am. Chem. Soc., 127: 11602-11603, 2005; Westrop G D, Goodall G, Mottram J C and Coombs G H, J. Biol. Chem., 281: 25062-25075, 2006) and that the OPSS of *M. tuberculosis*, can use $Na_2S$ as a sulfur donor in converting OPS to cysteine even in the absence of the additional enzymes when five C-terminal amino acid residues are removed therefrom (Argen D, Schnell R and Schneider G, FEBS letters, 583: 330-336, 2009). In the present invention, a microorganism is mutated to accumulate OPS therein, following incubation to convert OPS into cystein in the presence of the OPSS enzyme. Nowhere has this method been previously described.

Technical Solution

It is an object of the present invention to provide a method for producing cysteine or a derivative thereof. It is another object of the present invention to provide a recombinant microorganism for the production of O-phosphoserine.

Advantageous Effects

The method of the present invention in which O-phosphoserine is produced at high yield by a recombinant microorganism and is used for conversion into cysteine, as it is, is more friendly to the environment and ensures higher efficiency in the production of cysteine than do chemical synthesis methods. The cysteine and its derivatives produced by the fermentation and bioconversion of the present invention can be widely used in the production of animal and human foods and food additives.

BEST MODE

Figure 1:
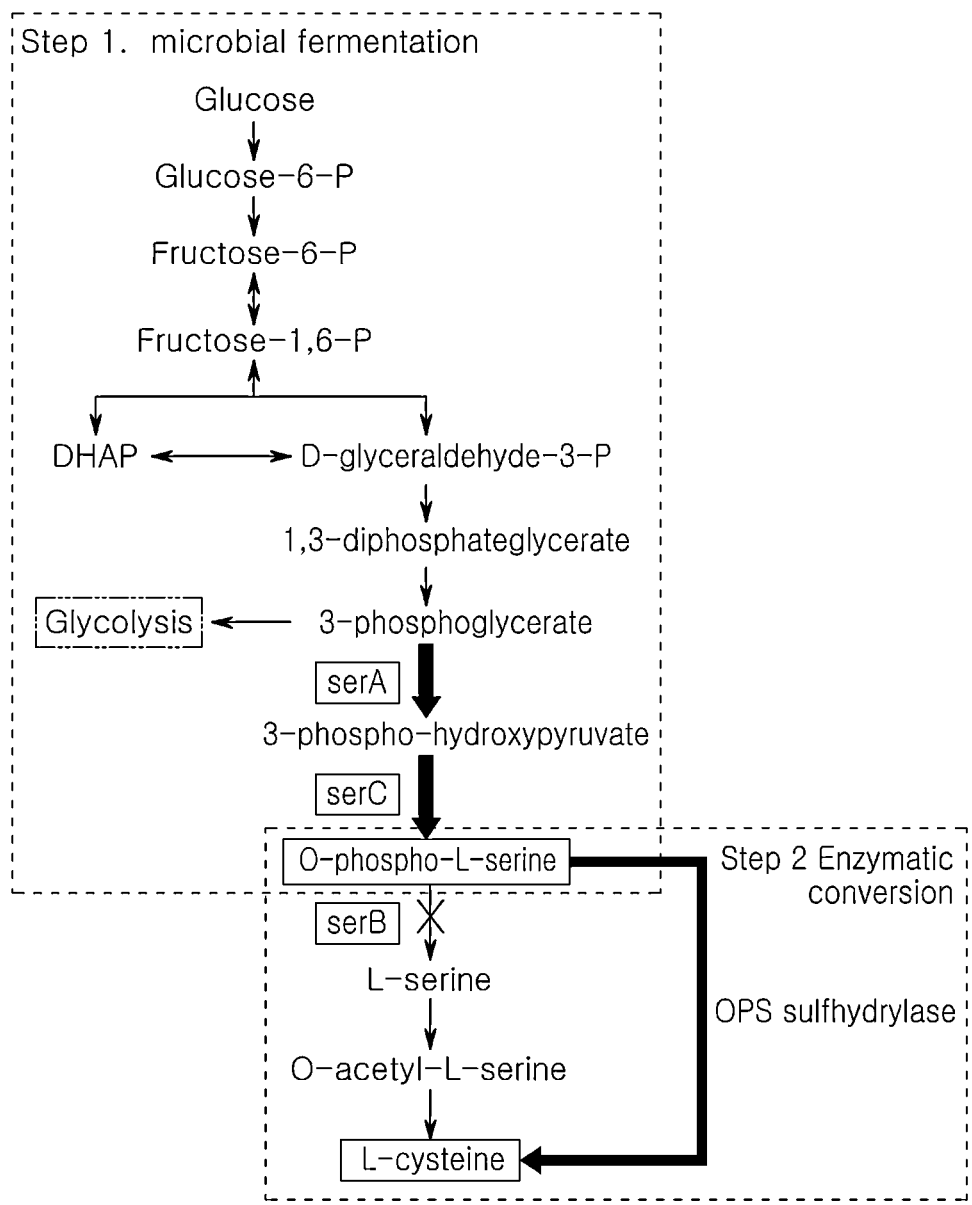
FIG. 1 is a schematic diagram showing the accumulation of O-phosphoserine by microbial fermentation and the enzymatic conversion of the accumulated O-phosphoserine into L-cysteine.

As used herein, the term "cysteine conversion" is intended to refer to the catalytic reaction of O-phosphoserine sulfhydrylase (OPSS) which results in the conversion of the substrate O-phosphoserine (OPS) into the product cysteine, that is, it refers to the catalytic reaction of converting OPS into cysteine.

As used herein, the term "cysteine conversion rate" refers to the percentage of the amount of the product cysteine to the amount of the starting material OPS. Under optimal reaction conditions, 1 mole of OPS is converted into 1 mole of cysteine. For example, if 100 moles of OPS is converted into 100 moles of cysteine, the cysteine conversion rate is 100%.

In accordance with an aspect thereof, the present invention provides a method for producing cysteine or a derivative thereof, comprising:

1) culturing a recombinant microorganism in which the activity of endogenous phosphoserine phosphatase (SerB) is reduced to produce O-sphosphoserine (OPS); and 2) reacting the OPS of step 1) with a sulfide in the presence of O-phosphoserine sulfhydrylase (OPSS) or a microorganism expressing OPSS, to produce cysteine or a derivative thereof.

The SerB is a protein that has the activity of hydrolyzing OPS into L-serine. Thus, a microorganism which has reduced endogenous SerB activity is characterized by the accumulation of OPS therein. The SerB is not limited to, may comprise any amino acid sequences, which exhibits SerB activity, and may have preferably the amino acid sequence of SEQ ID NO: 1 or 2. However, as long as it exhibits SerB activity, any amino acid sequence is used, which preferably has a homology of 90% or higher, more preferably 96% or higher, far more preferably 98% or higher, and most preferably 99% or higher with that of SEQ ID NO: 1 or 2. The reduced SerB activity means a decrease in SerB activity, compared to that of a prior-modified strain, and encompasses the disrupting of SerB. Various techniques for reduction of SerB activity are well known in the art. Illustrative examples include the deletion of a chromosomal serB, the introduction of mutation into the chromosomal serB to reduce endogenous SerB activity, the introduction of mutation into a regulatory region for the serB to reduce endogenous SerB activity, the substitution of the chromosomal serB with a gene mutated to reduce the endogenouse SerB activity and the introduction of an antisense oligonucleotide complementary to a transcript of the serB to inhibit the translation of the mRNA, but methods for reducing the SerB activity are not limited to these. These techniques may be applied to the reducing the activity of other enzymes in the present invention.

The disruption of endogenous SerB results in the introduction of serine auxotrophy into the recombinant microorganism so that the medium must be supplemented with glycine or serine. Glycine may be provided in the form of purified glycine, a glycine-containing yeast extract, or tryptone. Glycine is contained at a concentration of from 0.1 to 10 g/L, and preferably at a concentration of from 0.5 to 3 g/L. As for serine, it may be provided in the form of purified serine, a serine-containing yeast extract or tryptone. Its concentration in the culture medium ranges from 0.1 to 5 g/L, and preferably from 0.1 to 1 g/L.

In one embodiment of the present invention, when cultured in a glycine- or serine-containing medium, mutant *Corynebacterium glutamicum* or *E. coli* in which the activity of endogeneous SerB was disrupted was found to produce a higher amount of OPS, compared to the wild-type (see Tables 2, 3, 6 and 7).

In addition, the recombinant microorganism of the present invention may have enhanced phosphoglycerate dehydrogenase (SerA) or phosphoserine aminotransferase (SerC) activity. The SerA is a protein that has the activity of converting 3-phosphoglycerate to 3-phosphohydroxypyruvate. The SerA may have wild-type amino acids or a mutant amino acid sequence which shows resistance to feedback inhibition by serine, but is not limited to these. Preferably, the SerA may have one selected from the group consisting of amino acid sequences of SEQ ID NOS: 3 to 7. So long as it exhibits wild-type SerA activity or the mutant SerA activity resistant to serine feedback inhibition, any amino acid sequence may be used, although it preferably shares a homology of 90% or higher, more preferably 96% or higher, far more preferably 98% or higher, and most preferably 99% or higher with that of one of SEQ ID NO: 3 to 7. A "mutant SerA resistant to feedback inhibition" means the mutant showing a maintained or enhanced SerA activity irrespective of the feedback inhibition by serine or glycine. The feedback-resistant mutants are well known in the art (Grant G A et al., J. Biol. Chem., 39: 5357-5361, 1999; Grant G A et al., Biochem., 39: 7316-7319, 2000; Grant G A et al., J. Biol. Chem., 276: 17844-17850, 2001; Peters-Wendisch P et al., Appl. Microbiol. Biotechnol., 60: 437-441, 2002; EP0943687B). In one embodiment of the present invention, when a feedback-resistant serA was further introduced thereinto, *Corynebacterium glutamicum* or *E. coli* having a disrupted serB was found to produce a higher amount of OPS, as compared to the wild-type (see Tables 4 and 9).

The SerC is a protein that has the activity of converting 3-phosphohydroxypyruvate to O-phosphoserine. The SerC is not limited to, may comprise the sequences which exhibits SerC activity, and may have preferably the amino acid sequence of SEQ ID NO: 8. However, as long as it exhibits SerC activity, any amino acid sequence may be employed, but it should preferably share a homology of 90% or higher, more preferably 96% or higher, far more preferably 98% or higher, and most preferably 99% or higher with that of SEQ ID NO: 8. Furthermore, a mutation may be introduced into the serC so that the enzyme activity can be increased. In one embodiment of the present invention, when an serC was further introduced thereinto, *Corynebacterium glutamicum* or *E. coli* having a disrupted serB and a feedback-resistant serA was found to produce a higher amount of OPS, compared to the wild-type (see Table 9).

The enhancement of the enzyme activity may be achieved using various well-known methods, including, but not being limited to, increasing the copy number of a gene encoding an enzyme of interest, introducing a mutation into a regulatory region for the gene to enhance the enzyme activity, substituting the chromosomal gene with a gene mutated to enhance the enzyme activity, and introducing a mutation into the chromosomal gene to enhance the enzyme activity.

The recombinant microorganism of the present invention refers to any microorganism in which there is the reduction of SerB activity, thus producing OPS at an elevated level. If this condition is satisfied, any microorganism, whether prokaryotic or eukaryotic, falls within the scope of the present invention. Representative among them are enterobacteria or coryneform bacteria. Examples of the microorganisms useful in the present invention include *Escherichia* sp., *Erwinia* sp., *Serratia* sp., *Providencia* sp., *Corynebacterium* sp., and *Brevibacterium* sp. Preferable are *Escherichia* sp. and *Corynebacterium* sp, with more preference given for *Escherichia* sp. and with the highest preference being for *E. coli*.

In an embodiment, the recombinant strain capable of producing OPS was named *E. coli* CA07-0012, and deposited with the Korean Culture Center of Microorganisms, located at 361-221, Hongje 1, Seodaemun, Seoul, Korea, on Oct. 12, 2011 under accession number KCCM11212P.

In addition, in an embodiment, the recombinant strain capable of producing OPS was named *E. coli* CA07-0022/pCL-prmf-serA*(G336V)-serC, and deposited with the Korean Culture Center of Microorganisms, located at 361-221, Hongje 1, Seodaemun, Seoul, Korea, on Sep. 28, 2010 under accession number KCCM11103P. Herein, the term "CA07-0022/pCL-prmf-serA*(G336V)-serC" is used interchangeably with CA07-0022 serA*(G336V)/pCL-prmf-serA*(G336V)-serC.

As used herein, the term "culturing" is intended to mean growing microorganisms under artificially controlled conditions. A culturing procedure may be conducted using a suitable medium and culturing conditions well known in the art. Those skilled in the art can readily control the culturing procedure to correspond to the strains employed. For example, it may be performed in a batch type, in a continuous type, or in a fed-batch type, but is not limited thereto.

In addition, the culture medium contains a carbon source. Examples of the carbon source include saccharides and carbohydrates such as glucose, sucrose, lactose, fructose, maltose, starch and cellulose, oils and fats such as soybean oil, sunflower oil, castor oil and coconut oil, fatty acids such as palmitic acid, stearic acid and linoleic acid, alcohols such as glycerol and ethanol, and organic acids such as acetic acid. These carbon sources may be present solely or in combination in the culture medium. As a nitrogen source, an organic material such as peptone, yeast extract, meat juice, malt extract, corn steep liquor, soybean, and wheat protein, or an inorganic nitrogen compound such as urea, ammonium sulfate, ammonium chloride, ammonium phosphate, ammonium carbonate and ammonium nitrate may be contained in the culture medium. These nitrogen sources may be used solely or in combination. The medium may contain potassium dihydrogen phosphate, potassium phosphate, or corresponding sodium salts as a phosphorous source. The medium may contain metallic salts such as magnesium sulfate or iron sulfate. The culture medium may also contain amino acids, vitamins and suitable precursors. The nutrients may be added in a batch manner or a continuous manner to the medium.

A compound such as ammonium hydroxide, potassium hydroxide, ammonia, phosphoric acid and sulfuric acid may be added in a suitable manner to the culture medium during culturing to adjust the pH of the culture. In addition, during culturing, an anti-foaming agent such as fatty acid polyglycol ester is used to suppress the formation of foam. Further, in order to maintain the culture medium in an aerobic condition, oxygen or oxygen-containing gas can be injected into the culture medium. For an anaerobic or microaerobic condition, nitrogen, hydrogen, or carbon dioxide is provided without aeration. The culture medium may be typically maintained at a temperature of from 27° C. to 37° C. and preferably at a temperature of from 30° C. to 35° C. As for the culture period, it may be maintained until the product of interest is obtained in a desired amount, and preferably it ranges from 10 to 100 hours.

For further collection and recovery of the OPS produced during the culturing step from the culture medium, a suitable method well known in the art may be selected depending on the type of culture, be it a batch, continuous or fed-batch culture.

In the method of the present invention, step 2) addresses the reaction of the OPS of step 1) with a sulfide in the presence of O-phosphoserine sulfhydrylase (OPSS) or a microorganism expressing OPSS, to induce the conversion of O-phosphoserine into cysteine or its derivatives.

The sulfide may be provided in a liquid or gas form as well as in a solid form typically used in the art, because of the difference in pH, pressure and/or solubility. So long as it may be converted to a thiol group (SH), any sulfur compound such as sulfide ($S^{2-}$) or thiosulfate ($S_2O_3^{2-}$) may be used in the present invention. Preferably, $Na_2S$, NaSH, $H_2S$, $(NH_4)_2S$, NaSH and $Na_2S_2O_3$, all of which can provide a thiol group for OPS, may be used. In the reaction, one thiol group is supplied to one OPS molecule to afford one molecule of cysteine or a derivative thereof. In this enzymatic conversion, a sulfide may be preferably added at a molar concentration 0.1 to 3 times and more preferably 1 to 2 times as high as that of OPS used. In light of the economy, a thiol group-providing sulfide and OPS are most preferably used at a molar ratio of 1:1. In one embodiment of the present invention, $Na_2S$ was used as the source of sulfur. $Na_2S$ was added at a molar concentration 1 to 3 times as high as that of OPS used in the conversion reaction. Preferably, it is fed at a molar concentration twice as high as that of OPS to effectively convert OPS into cysteine (Table 18).

As used herein, the term "O-phosphoserine sulfhydrylase (OPSS)" refers to an enzyme that catalyzes the transfer of a thiol group (SH) to OPS (O-phosphoserine) to convert OPS into cysteine. The enzyme was first found in *Aeropyrum pernix, Mycobacterium tuberculosis*, and *Trichomonas vaginalis* (Mino K and Ishikawa K, FEBS letters, 551: 133-138, 2003; Burns K E et al., J. Am. Chem. Soc., 127: 11602-11603, 2005). The above mentioned enzymes have the amino acid sequences of SEQ ID No: 9 and 12.

As used herein, the term "mutant" refers to a culture or an individual that shows an inheritable or non-heritable alteration in phenotype. When used in conjunction with OPSS, the term "mutant" is intended to mean an OPSS enzyme which is genetically altered such that its activity can be effectively enhanced, compared to the wild-type.

In the present invention, the OPSS mutant can be constructed by deleting, substituting or adding a part of a nucleotide sequence encoding OPSS. According to one embodiment of the present invention, an OPSS enzyme with enhanced activity was prepared by deleting five C-terminal amino acid residues of the OPSS enzyme of *Mycobacterium*

*smegmatis*. The mutant enzymes have the amino acid sequences of SEQ ID NO: 10 and 11.

The OPSS mutant can be obtained in *E. coli*, widely used for enzyme expression, using gene synthesis techniques based on codon optimization by which enzymes of interest can be obtained in high yield. Alternatively, screening methods of useful enzyme resources based on the bioinformatics of massive amounts of genetic information about microorganisms may be used to obtain the OPSS mutant. In one embodiment of the present invention, OPSS enzymes that utilize OPS as a substrate to synthesize cysteine were selected from various microbes by screening the homology of amino acid sequences. In this regard, cell pellets obtained using a medium and culture conditions that were suitable in the art were lyzed, followed by the purification of the supernatant containing the enzyme to afford the OPSS enzyme (Table 10).

In addition, a high-yield expression system was developed for obtaining the OPSS enzyme economically. A pET vector employing a T7 promoter is well known in the art. However, the present inventors developed an enzyme expression system, named the CJ1 system (Korean Patent 10-0620092 B1), instead of employing the typical system. In one embodiment of the present invention, the expression levels of OPSS between a pET system comprising a T7 promoter and the CJ1 system comprising a CJ1 promoter were compared given the same conditions. As a result, the CJ1 system showed a higher expression level of OPSS than the pET system. In addition, the overexpression of OPSS required a low temperature (18° C.) and a long period of time in the pET system, but a high temperature (37° C.) and a short period of time in the pCL-pCJ1 system. Preferably, the pCL-pCJ1 system is used to obtain OPSS (Example 20).

The enhancement of the enzyme activity may be achieved using various well-known methods. For example, it can be performed by increasing the number of copies of a gene encoding OPSS, using a strong promoter, or introducing a genetic mutation.

Optimization of the enzymatic conversion of OPSS may be achieved using various methods known in the art. For example, the optimization may be based on a full understanding of the characteristics of OPSS, such as the optimal temperature and pH, inhibition against substrates, substrate concentration, heat stability, etc. In addition, the optimization may be determined by optimal conditions for the enzymatic conversion, such as the optimal OPSS concentration, the optimal balances of the substrates used in terms of concentrations, a preference for sulfur compounds providing SH for the enzymatic conversion, a preference for certain buffers, the influence of ions generated, and cofactors and their optimal concentrations.

In one embodiment of the present invention, the OPSS enzyme obtained using the above-mentioned method was characterized and on the basis of the determined characteristics, an economically beneficial enzymatic conversion process that has a high conversion rate of cysteine from OPS, with the guarantee of enzyme stability, was developed. In the enzymatic conversion process, the reaction temperature can be set from 37° C. to 80° C. In detail, Ape-OPSS (SEQ ID NO: 12), belonging to Archea, exhibits increased enzymatic activity at 60° C. compared to 37° C., and the enzyme itself is highly stable to heat, with optimal reactivity at 60° C. On the other hand, Msm-T (SEQ ID NO: 10) exhibits optimal activity at 37° C. and is relieved the activity to heat treatment at 60° C. The OPSS enzyme was observed to have enzymatic activity over a pH range of 6.0 to 10.0. Ape-OPSS showed optimal activity at pH 7.4. With the appearance of optimal activity at a pH of from 8.0 to 9.0, Msm-T showed stability over a wider pH range, compared to Ape-OPSS (Tables 12 and 15, and FIGS. 2 and 3).

As a cofactor, 0.001-2 mM PLP (pyridoxal-5'-phosphate) or 0.001-100 mM DTT may be used in the enzymatic conversion. In one embodiment of the present invention, the cysteine conversion rate was 2.3-fold increased in the presence of 25 mM DTT or 0.2 mM PLP. As such, treatment with DTT or PLP brought about an improvement in the cysteine conversion rate of step 2). The addition of the cofactor was set to a reasonable level in consideration of the increased production cost and the increased conversion rate (Table 14).

Figure 5:
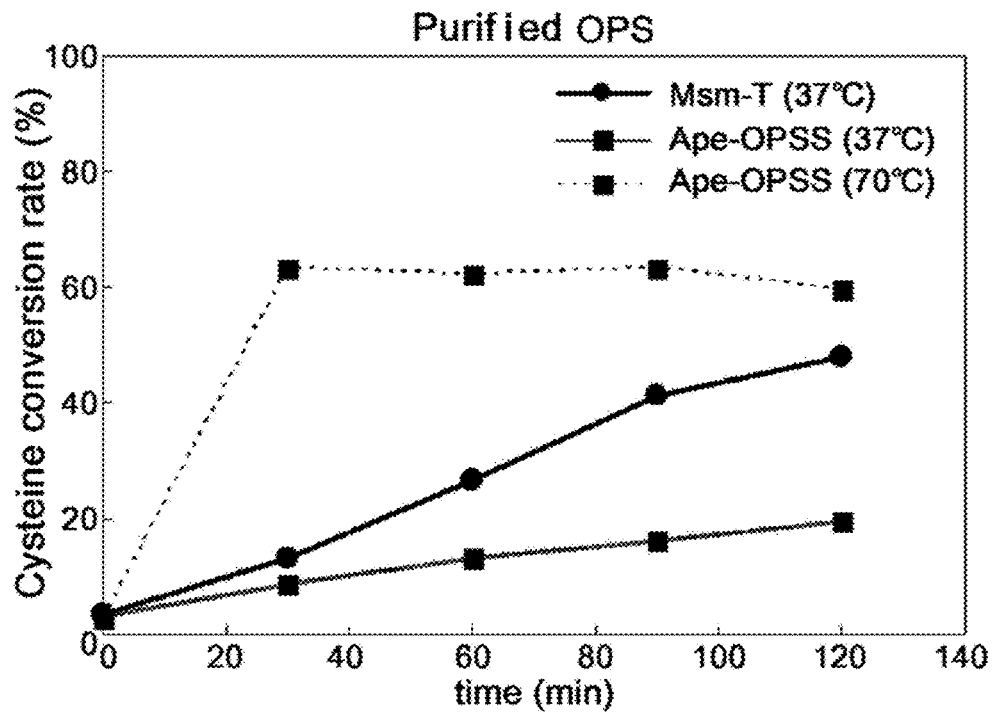
FIG. 5 is a graph showing the enzymatic activity of OPS sulfhydrylase to convert purified OPS fermentation broth into cysteine.
Figure 6:
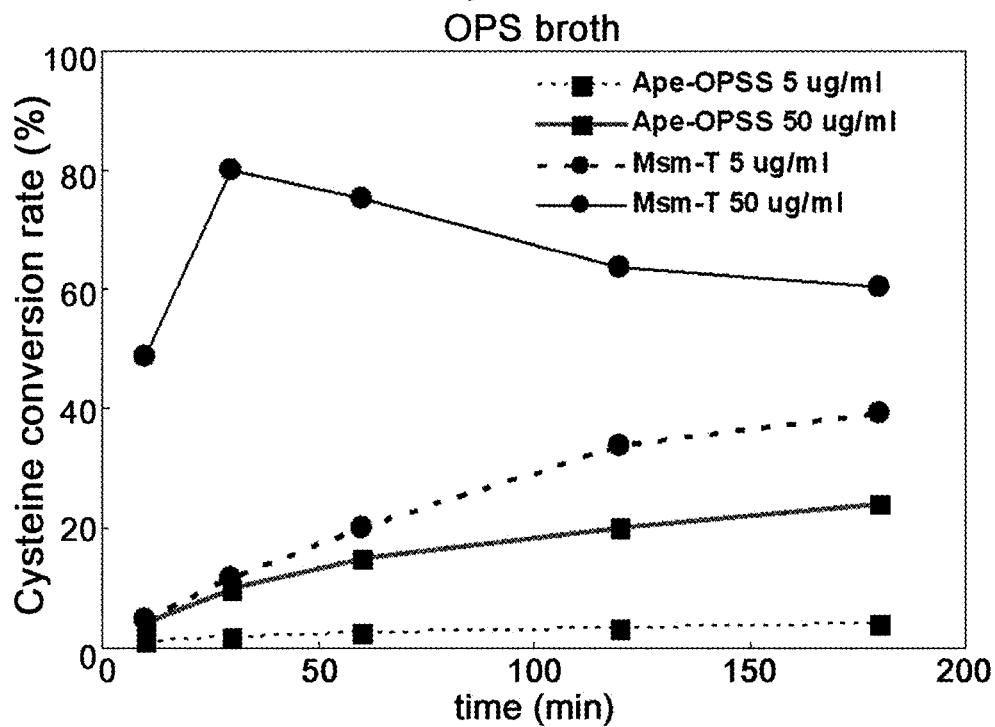
FIG. 6 is a graph showing the enzymatic activity of OPS sulfhydrylase to convert OPS fermentation broth into cysteine.

The reaction conditions for OPSS may vary depending on the kinds and concentration of the OPS used. In one embodiment of the present invention, pure OPS (commercially available), OPS purified from the culture prepared in step 1), and the OPS-containing culture of step 1) were used under various conditions to provide the optimal conversion rates. As a result, the cysteine conversion rate varied depending on the kind and concentration of OPSS and the reaction temperature and the kind and concentration of OPS (FIGS. 5 and 6, and Table 19).

The method of the present invention may further comprise isolating and purifying the cysteine produced in step 2). After the enzymatic conversion, cysteine can be isolated and purified from the culture medium using a method well known in the art.

Those skilled in the art may chemically synthesize cysteine derivatives from cysteine using a well known method. Cysteine may be readily reacted with an acetylation agent to give NAC (N-acetylcysteine) and with haloacetic acid under basic conditions to give SCMC (S-carboxymetylcysteine). These cysteine derivatives are used as materials in medicines that treat coughs, bronchitis, bronchial asthma, and sore throat.

In the present invention, the OPS broth obtained through microbial fermentation is used as a substrate for synthesizing cysteine. The OPS broth obtained by microbial fermentation has economical advantages over commercially available pure OPS in that the OPS broth can be used without having to be additionally purified and the cofactor PLP necessary for the conversion can be obtained from the fermented culture.

In one embodiment of the present invention, a conversion process was developed which ensures a cysteine conversion rate of as high as 80% when 50 µg/ml Msm-T was used under reaction conditions of a 50 mM OPS broth or a 60 mM purified OPS broth, 100 mM $Na_2S$ or 120 mM $Na_2S$, and 0.2 mM PLP. It should be appreciated to those skilled in the art that the enzymatic conversion using highly active enzymes can easily be optimized and scaled up.

In accordance with another aspect thereof, the present invention provides a recombinant microorganism which is reduced the activity of SerB for the production of OPS. In one embodiment, the recombinant microorganism shows an enhancement of serine feedback-resistant serA or serC or deletion of at least one selected from among PhnC/PhnD/PhnE alkylphosphonate ABC transporter (phnCDE operon), alkaline phosphatase (phoA) and acid phosphatase (aphA). Preferably, the recombinant microorganisms for the production of OPS are the microorganism deposited under accession No. KCCM11103P or KCCM11212P. More preferably, the recombinant microorganism for the production of OPS is the microorganism deposited under accession No. KCCM11103P.

Mode for Invention

A better understanding of the present invention may be obtained through the following examples which are set forth to illustrate, but are not to be construed to limit the present invention.

<Preparation of O-Phosphoserine Producing *Corynebacterium* and Production of O-Phosphoserine Using the Same>

Example 1

Preparation of Phosphoserine Phosphatase (serB) Deficient *Corynebacterium* Strain

*Corynebacterium glutamicum* 13032 was modified by deleting the serB gene (SEQ ID NO: 13, EC 3.1.3.3) encoding phosphoserine phosphatase, which catalyses the synthesis of L-serine from O-phosphoserine, therefrom. To this end, a fragment for inactivation of serB was constructed. In this regard, primers were designed for the preparation of the recombinant strain 13032-ΔserB of the present invention. First, the serB sequence of *Corynebacterium glutamicum* 13032 was obtained with reference to the data of the NIH GenBank, and primers SEQ ID NOS: 22 to 27 were synthesized on the basis of the serB sequence. For the site-specific gene disruption, a pDC vector which cannot replicate in *Corynebacterium glutamicum* was employed. A pDC-ΔserB plasmid in which the open reading frame of serB was internally disrupted was constructed and adopted for the preparation of a site-specific serB gene deletion in *Corynebacterium glutamicum* mutant strain. The internal gene distruption of the pDC-ΔserB was generated by crossover PCR using primer pairs of SEQ ID NOS: 22 and 23 and SEQ ID NOS: 24 and 25, with the genomic DNA of *Corynebacterium glutamicum* ATCC13032 serving as a template, and introducing the PCR product into a pDC vector. The resulting recombinant plasmid was transformed into wild-type *Corynebacterium glutamicum* by electroporation (van der Rest et al. 1999). The plasmid was introduced into the chromosome by primary recombination (crossing over), followed by secondary recombination (crossing over) to excise the original serB from the chromosome.

After completion of the secondary recombination, the *Corynebacterium glutamicum* transformants containing the deletion mutation of serB was analyzed by diagnostic PCR using a pair of gene-specific primers SEQ ID NOS: 26 and 27. The recombinant strain was named CB01-0047.

Example 2

Assay for O-Phosphoserine Productivity in the Phosphoserine Phosphatase Deficient *Corynebacterium* Strain The mutant strain CB01-0047, resulting from the deletion of serB from *Corynebacterium glutamicum* 13032, which was anticipated to accumulate O-phosphoserine, was spread over BHIS plates and incubated overnight in a 30° C. incubator. Afterwards, the colonies appearing on the BHIS plates were inoculated in 25 mL of a titer medium shown in Table 1 using a platinum loop and then incubated at 30° C. for 48 hours with shaking at 200 rpm. The results are summarized in Table 2, below.

TABLE 1

| Composition | Amount (per liter) |
|---|---|
| Glucose | 100 g |
| KH$_2$PO$_4$ | 1.1 g |
| (NH$_4$)$_2$SO$_4$ | 45 g |
| MgSO$_4$.7H$_2$O | 1.2 g |
| HSM | 20 g |
| Trace elements | 20 ml |

TABLE 1-continued

| Composition | Amount (per liter) |
|---|---|
| Calcium carbonate | 30 g |
| pH | 7.2 |
| Trace elements | |
| Biotin | 0.09 g |
| Thiamine | 0.45 g |
| Ca-Panthenate | 0.45 g |
| NCA | 3 g |
| FeSO$_4$.7H$_2$O | 9 g |
| MnSO$_4$.4H$_2$O | 9 g |
| ZnSO$_4$.7H$_2$O | 0.045 g |
| CuSO$_4$.5H$_2$O | 0.045 g |

TABLE 2

| Strain | OD 562 nm | Sugar consumed (g/L) | O-phosphoserine (g/L) |
|---|---|---|---|
| C. glutamicum 13032 | 25 | 100 | 0.02 |
| CB01-0047 | 6.5 | 23 | 0.07 |

The CB01-0047 strain was observed to grow very slowly in the titer medium. This growth retardation was not improved even upon the addition of an L-glycine supplement. However, the growth was increased in the presence of L-serine, but a slight increase in the production of O-phosphoserine compared to the wild-type was observed. The results are summarized in Table 3, below.

TABLE 3

| Strain | A.A. (amino acids) added | OD 562 nm | Sugar consumed (g/L) | O-phosphoserine (g/L) |
|---|---|---|---|---|
| CB01-0047 | — | 6.3 | 21 | 0.09 |
| | L-Glycine | 6.9 | 22 | 0.09 |
| | L-Serine | 24.5 | 100 | 0.05 |

Example 3

Construction of Mutated Phosphoglycerate Dehydrogenase (SerA*) Gene Derived from *Corynebacterium*

The *Corynebacterium glutamicum*-derived genes serA* (E235K) (SEQ ID NO: 14) and serA*(197Δ) (SEQ ID NO: 15) were constructed, which encode respective mutants of 3-phosphoglycerate dehydrogenase, an enzyme catalyzing the synthesis of 3-phosphohydroxypyruvate from 3-phosphoglycerate. The mutants were reported to be feedback resistant (FBR) to serine (Peters-Wendisch P et al., Appl. Microbiol. Biotechnol., 60: 437-441, 2002; EP0943687B). serA* (E235K) was obtained by sewing PCR on the genomic DNA of ATCC13032 using primers of SEQ ID NOS: 28 to 31 while serA*(197Δ) was constructed by PCR using pairs of primers of SEQ ID NOS: 28 to 32. The PCR products thus obtained were inserted into respective T vectors to construct recombinant vectors called Tblunt-serA*(E235K) and Tblunt-serA* (197Δ). Subsequently, the two vectors were treated with restriction enzymes EcoRV and XbaI to give two DNA fragments serA*(E235K) and serA*(197Δ). These fragments were inserted to respective pECCG117-Pcj7-GFP-terminator vectors which had been disgested with the same restriction enzymes. As a result, two recombinant vectors pECCG117-Pcj7-serA*(E235K), and pECCG117-Pcj7-serA*(197Δ) were obtained.

Example 4

Preparation of serA* Overexpressing Corynebacterium Strain and Assay for O-Phosphoserine Productivity The two Corynebacterium-derived FBR-serA* plasmids constructed in Example 3 were introduced into Corynebacterium glutamicum CB01-0047. To evaluate O-phosphoserine productivity, the transformants were spread over BHIS plates and incubated overnight at 30° C. Afterwards, the colonies appearing on the BHIS plates were inoculated in 25 mL of a titer medium shown in Table 1 additionally contained 2 g/L L-serine using a platinum loop and then incubated at 30° C. for 48 hours with shaking at 200 rpm. The results are summarized in Table 4, below.

TABLE 4

| Strain | OD 562 nm | Sugar consumed (g/L) | O-phosphoserine (g/L) |
|---|---|---|---|
| CB01-0047/pECCG117 | 24.5 | 100 | 0.03 |
| CB01-0047/pECCG117-Pcj7-serA*(E235K) | 25.3 | 100 | 0.3 |
| CB01-0047/pECCG117-Pcj7-serA*(197Δ) | 24.3 | 100 | 0.28 |

In the Corynebacterium glutamicum strains transformed with the corynebacterium-derived FBR-serA*, as shown in Table 4, The accumulations of O-phosphoserine at a concentration of from 0.1 to 0.3 g/L were observed.

<Preparation of O-Phosphoserine Producing E. coli and Production of O-Phosphoserine Using the Same>

Example 5

Preparation of E. coli Strain Having the Reduced Activity of Phosphoserine Phosphatase (SerB)

E. coli was modified by deleting the serB gene (SEQ ID NO: 16) encoding phosphoserine phosphatase, which catalyses the synthesis of L-serine from O-phosphoserine, therefrom. The deletion mutant E. coli K12 was prepared using the one-step inactivation method (Datsenko K A and Wanner B L, Proc. Natl. Acad. Sci., 97: 6640-6645, 2000) to delete an antibiotic-resistant maker gene. To prepare the serB deletion strain, first, PCR was performed on a pKD3 plasmid (Datsenko K A and Wanner B L, Proc. Natl. Acad. Sci., 97: 6640-6645, 2000; GenBank No. AY048742) using a pair of primers of SEQ ID NOS: 33 and 34. The PCR product was (introduced into competent cells of pKD46 containing E. coli K12 (Datsenko K A and Wanner B L, Proc. Natl. Acad. Sci., 97: 6640-6645, 2000; GenBank No. AY048746) by electroporation. Thereafter, strains that showed resistance to chloramphenicol were subjected to PCR to confirm the deletion of serB, and then transformed with pCP20 (Datsenko K A and Wanner B L, Proc. Natl. Acad. Sci., 97: 6640-6645, 2000) to remove the antibiotic-resistant marker. The resulting mutant strain was named CA07-0012.

In addition, the initiation codon of serB was modified to lower phosphoserine phosphatase activity as follows. The wild-type serB gene with ATG as an initiation codon was obtained by PCR with the genomic DNA of E. coli W3110 serving as a template. A mutant serB with CTG as an initiation codon was constructed by sewing PCR. A pair of primes of SEQ ID NOS: 35 and 36 was used in the PCR for amplifying the wild-type serB while pairs of primers of SEQ ID NOS: 37 to 38 were employed for PCR amplification of the mutant serB. The PCR products was treated with HindIII and cloned into pccBAC1 (Epicentre) at the HindIII restriction site to construct pccBAC1-Pself-ATG-serB, and pccBAC1-Pself-CTG-serB respectively. The wild-type and the mutant serB vector was introduced into CA07-0012 to compare the phosphoserine phosphatase activity.

Example 6

Assay of Strain Having the Reduced Activity of SerB for O-Phosphoserine Productivity The phosphoserine phosphatase deficient mutant strain CA07-0012 that was anticipated to accumulate O-phosphoserine, was spread over LB plates and incubated overnight in a 33° C. incubator. Afterwards, the colonies appearing on the LB plates were inoculated in 25 mL of a titer medium shown in Table 5 using a platinum loop and then incubated at 33° C. for 48 hours with shaking at 200 rpm. The results are summarized in Table 6, below.

TABLE 5

| Composition | Amount (per liter) |
|---|---|
| Glucose | 40 g |
| $KH_2PO_4$ | 2 g |
| $(NH_4)_2SO_4$ | 17 g |
| $MgSO_4 \cdot 7H_2O$ | 1 g |
| $FeSO_4 \cdot 7H_2O$ | 10 mg |
| $MnSO_4 \cdot 4H_2O$ | 10 mg |
| $ZnSO_4 \cdot 7H_2O$ | 10 mg |
| Yeast extract | 2 g |
| Calcium carbonate | 30 g |
| pH | 6.8 |

TABLE 6

| Strain | OD 562 nm | Sugar consumed (g/L) | O-phosphoserine (g/L) |
|---|---|---|---|
| E. coli W3110 | 16 | 40 | 0.03 |
| CA07-0012 | 9.8 | 16 | 0.5 |
| CA07-0012/pccBAC1-Pself-ATG-serB | 20 | 40 | 0 |
| CA07-0012/pccBAC-Pself-CTG-serB | 15 | 40 | 0.7 |

To enhance the growth and O-phosphoserine productivity thereof, CA07-0012 was cultured for 48 hours in the titer medium of Table 5 additionally contained 1 g/L L-glycine. The results are summarized in Table 7, below.

TABLE 7

| Strain | OD 562 nm | Sugar consumed (g/L) | O-phosphoserine (g/L) |
|---|---|---|---|
| E. coli W3110 | 16 | 40 | 0.03 |
| CA07-0012 | 18 | 40 | 1.5 |

As shown in Table 7, the addition of L-glycine to the culture medium allowed the strain to increase the growth rate and the O-phosphoserine productivity.

Example 7

Construction of the Vector Harvoring the Mutated Phosphoglycerate Dehydrogenase (SerA*) Gene derived from *E. coli*

The *E. coli*-derived genes serA*(G336V) (SEQ ID NO: 18), serA*(G336V, G337V) (SEQ ID NO: 19), and serA* (G336V, R338G) (SEQ ID NO: 20) encoding respective mutants of 3-phosphoglycerate dehydrogenase, an enzyme catalyzing the synthesis of 3-phosphohydroxypyruvate from 3-phosphoglycerate were constructed. The mutants were reported to be feedback resistant (FBR) to serine (Grant G A, Xu X L and Hu Z, Biochem., 39: 7316-7319, 2000; Grant G A, Hu Z and Xu X L, J. Biol. Chem., 276: 17844-17850, 2001). The introduction of the mutant genes into the chromosome of *E. coli* was carried out using the sewing PCR method. The DNA fragments containing mutations were prepared using following primers.

Primers of SEQ ID NOS: 39 and 41 were used commonly in SerA* gene. To introduce mutations into the serA gene, PCR was performed with a pair of primers of SEQ ID NOS: 42 and 43 for serA*(G336V), with a pair of primers of SEQ ID NOS: 44 and 45 for serA*(G336V, G337V), and with a pair of primers of SEQ ID NOS: 46 and 47 for serA*(G336V, R338G). The primers were synthesized on the basis of information about the K12 W3110 gene (GenBank accession number AP 003471) and its neighboring nucleotide sequences, registered in the NIH GenBank.

Example 8

Cloning of *E. coli*-Derived serA Gene, serA* Gene, and 3-Phosphoserine Aminotransferase (serC) Gene serA (SEQ ID NO: 17, EC 1.1.1.95), serC (SEQ ID NO: 21, EC 2.6.1.52), serA*(G336V), serA*(G336V, G337V) and serA*(G336V, R338G) were cloned as follows. serA and serC were obtained by performing PCR on the genomic DNA of *E. coli* W3110 while serA*(G336V), serA*(G336V, G337V), and serA*(G336V, R338G) were constructed by PCR with the DNA fragments of Example 7 serving as templates. PCR primers were SEQ ID NOS: 48 and 49 for serA and SEQ ID NOS: 50 and 51 for serC. After treatment with EcoRV and HindII, the PCR products were cloned into the recombinant vector pCL-Prmf, constructed by inserting the *E. coli* rmf promoter into the pCL1920 vector (GenBank No AB236930) to produce respective recombinant vectors named pCL-Prmf-serA, pCL-Prmf-serC, pCL-Prmf-serA*(G336V), pCL-Prmf-serA*(G336V, G337V), and pCL-Prmf-serA*(G336V, R338V) respectively.

In addition, plasmids in which serA, one of the three serA mutants, and/or serC form an operon, that is, pCL-Prmf-serA-(RBS)serC, pCL-Prmf-serA*(G336V)-(RBS)serC, pCL-Prmf-serA*(G336V, G337V)-(RBS)serC, and pCL-Prmf-serA*(G336V, R338V)-(RBS)serC were constructed. In this regard, an (RBS)serC fragment was obtained using primers of SEQ ID NOS: 51 and 52 and cloned at a HindIII site into pCL-Prmf-serA, pCL-Prmf-serA*(G336V), pCL-Prmf-serA*(G336V, G337V), and pCL-Prmf-serA*(G336V, R338V).

Example 9

Preparation of *E. coli*-Derived serA, serA* and serC Enhanced Strains and Assay for O-Phosphoserine Productivity The eight plasmids constructed in Example 8 were transformed into CA07-0012 and the resulting recombinant strains were assayed for the productivity of O-phosphoserine. Each strain was spread over LB plates and incubated overnight at 33° C. Afterwards, colonies appearing on the LB plates were inoculated into 25 mL of titer media of Table 8 and cultured at 33° C. for 48 hours with shaking at 200 rpm. The results are summarized in Table 9, below.

TABLE 8

| Composition | Amount (per liter) |
|---|---|
| Glucose | 40 g |
| $KH_2PO_4$ | 4 g |
| $(NH_4)_2SO_4$ | 17 g |
| $MgSO_4 \cdot 7H_2O$ | 1 g |
| $FeSO_4 \cdot 7H_2O$ | 10 mg |
| $MnSO_4 \cdot 4H_2O$ | 10 mg |
| $ZnSO_4 \cdot 7H_2O$ | 10 mg |
| L-Glycine | 2.5 g |
| Tryptone | 2 g |
| Yeast extract | 2 g |
| Calcium carbonate | 30 g |
| pH | 6.8 |

TABLE 9

| Strain | OD 562 nm | Sugar consumed (g/L) | O-phosphoserine (g/L) |
|---|---|---|---|
| CA07-0012 | 23 | 40 | 1.7 |
| CA07-0012/pCL-Prmf-serA | 25 | 40 | 1.8 |
| CA07-0012/pCL-Prmf-serA*(G336V) | 23 | 37 | 2.2 |
| CA07-0012/pCL-Prmf-serA*(G336V, G337V) | 21 | 36 | 2.1 |
| CA07-0012/pCL-Prmf-serA*(G336V, R338V) | 22 | 37 | 2.2 |
| CA07-0012/pCL-Prmf-serA-(RBS)serC | 20 | 35 | 2.1 |
| CA07-0012/pCL-Prmf-serA*(G336V)-(RBS)serC | 18 | 31 | 2.5 |
| CA07-0012/pCL-Prmf-serA*(G336V, G337V)-(RBS)serC | 17 | 32 | 2.5 |
| CA07-0012/pCL-Prmf-serA*(G336V, R338V)-(RBS)serC | 16 | 30 | 2.6 |

As apparent from the data of Table 9, the *E. coli* CA07-0012 strain increased in the productivity of O-phosphoserine when it was transformed with serA, and the productivity of O-phosphoserine was increased to a greater extent upon the introduction of one of the three serA* mutants. The strains in which serA, or one of three serA* mutants and serC that were activated simultaneously showed higher productivity of O-phosphoserine than did those in which there was the sole activation of serA or serA*. The highest productivity of O-phosphoserine was detected in a strain in which the mutant serA* and serC were activated simultaneously.

<Development and Characterization of O-Phosphoserine (OPS) Sulfhydrylase (OPSS)>

Example 10

Development of OPS Sulfhydrylase (OPSS)

*Aeropyrum pernix, Mycobacterium tuberculosis*, and *Trichomonas vaginalis* are reported to have O-phosphoserine sulfhydrylase (OPSS), an enzyme that employs O-phospho-L-serine (OPS), instead of O-acetyl serine (OAS) in *E. coli*, as a substrate for the synthesis of cysteine (Mino K and Ishikawa K, FEBS letters, 551: 133-138, 2003; Burns K E, Baumgart S, Dorrestein P C, Zhai H, McLafferty F W and Begley T P, J. Am. Chem. Soc., 127: 11602-11603, 2005; Westrop G D, Goodall G, Mottram J C and Coombs G H, J. Biol. Chem., 281: 25062-25075, 2006). Based on the report, the present inventors found two types of OPS sulfhydrylase, which converts OPS into cysteine, from *Aeropyrum pernix* and *Mycobacterium tuberculosis* H37Rv. Of them, the *Mycobacterium tuberculosis* H37Rv-derived OPSS enzyme was used for screening amino acid homology. As a result, three types of OPSS were secured from *Mycobacterium smegmatis* str. MC2 155, *Rhodococcus jostii* RHA1, and *Nocardia farcinica* IFM 10152.

To obtain OPSS from each strain, a pET28a vector system (Novagen), which is typically used for enzyme expression, was constructed. Each templates and primers for use in cloning the five different OPS sulfhydrylase genes and the resulting recombinant plasmids are summarized in Table 10, below. Suitable combinations of the templates and the primers, as given in Table 10, were used for PCR for amplifying respective OPSS genes. The PCR products and the pET28a vector were digested with NdeI and HindIII (37° C. for 3 hours). Each of the gene fragments was ligated to the digested pET28a vector (Novagen). Base sequencing confirmed the construction of the expression vectors carrying the each OPSS genes. The enzyme expression vectors were introduced into *E. coli* (DE3) to produce strains capable of expressing five OPSS enzymes. Enzyme names are given in Table 10, below.

TABLE 10

| Enzyme | Vector | Template | Primer |
|---|---|---|---|
| Ape-OPSS | pET28a-Ape-OPSS | Synthetic DNA | SEQ ID NOS: 53 and 54 |
| Mtb-OPSS | pET28a-Mtb-OPSS | Mtb Genomic DNA | SEQ ID NOS: 55 and 56 |
| Msm-OPSS | pET28a-Msm-OPSS | Msm Genomic DNA | SEQ ID NOS: 57 and 58 |
| Rjo-OPSS | pET28a-Rjo-OPSS | Rjo Genomic DNA | SEQ ID NOS: 59 and 60 |
| Nfa-OPSS | pET28a-Nfa-OPSS | Nfa Genomic DNA | SEQ ID NOS: 61 and 62 |

Expression of the enzymes was conducted according to the instructions of the pET system manufacturer (Novagen). Single colonies of each strain from the LB plates were inoculated into 5 mL of LB broth and incubated at 37° C. for 16 hours while shaking at 200 rpm. The cultures were transferred to 25 mL of fresh LB broth (in 250 mL flasks) and incubated to an $OD_{600}$ of 0.5-0.6 (for 2-3 hours) in the same condition, immediately after which 1 mM IPTG was added to the media to induce the enzymes to be expressed during incubation at 18° C. for 18 hours while shaking at 120 rpm.

The enzymes were purified using Ni-NTA columns with His-tag, with the aid of His SpinTrap (GE Healthcare). Of the five OPSS enzymes thus isolated, four were found to be in soluble forms, with one (Rjo-OPSS) being an inclusion body, as analyzed by 14% SDS-PAGE electrophoresis.

Example 11

Assay of OPS Sulfhydrylase (OPSS) for Cysteine Synthesis Activity

The OPS sulfhydrylase enzymes obtained from the four microorganism strains were assayed for ability to catalyze the conversion of O-phosphoserine (OPS) to cysteine. With regard to assay conditions and methods (cysM enzyme assay), reference was made to previous reports (Mino K and Ishikawa K, FEBS letters, 551: 133-138, 2003; Burns K E, Baumgart S, Dorrestein P C, Zhai H, McLafferty F W and Begley T P, J. Am. Chem. Soc., 127: 11602-11603, 2005; Westrop G D, Goodall G, Mottram J C and Coombs G H, J. Biol. Chem., 281: 25062-25075, 2006). The amount of the substrate used is represented by a unit of mL. Assay conditions for enzyme activity are summarized in Table 11, below.

TABLE 11

| Stock soln | Final Conc. | Blank | OPS sulfhydrylase |
|---|---|---|---|
| 6x his-enzyme | — | — | 40 (50 mg) |
| 1M HEPES(pH7.4) | 100 mM HEPES | 100 | 100 |
| 0.5M $Na_2S$ | 10 mM $Na_2S$ | 20 | 20 |
| 10 mM PLP | 0.2 mM PLP | 20 | 20 |
| 100 mM OPS | 5 mM OPS | 0 | 50 |
| DW | | 790 | 750 |
| Total | | 1000 | 1000 |

Reaction solutions excepting of the enzymes were incubated at 37° C. for 5 min, after which 50 mg of purified OPS sulfhydrylase was added to the reaction solution. At predetermined times during incubation at 37° C., 100 mL of the enzyme reactions was taken and mixed with 100 mL of 33.2% TCA to stop the enzymatic reaction. The cysteine concentrations of the enzyme reactions were quantitatively analyzed by measuring absorbance at $OD_{560}$ according to the Gaitonde method. Cysteine synthesis activities of the four different OPS sulfhydrylase enzymes are summarized in Table 12, below. The cysteine synthesis titers of the OPSS enzymes are expressed as cysteine conversion rates with reaction time.

TABLE 12

| | Cysteine Conversion Rate (%) | | |
|---|---|---|---|
| | 10 min | 30 min | 60 min |
| Ape-OPSS | 63.4 | 89.7 | 97.4 |
| Mtb-OPSS | 1.7 | 4.8 | 10.1 |
| Msm-OPSS | 12.8 | 25 | 43.7 |
| Nfa-OPSS | 0.1 | 0.1 | 0.2 |

The OPS sulfhydrylase enzymes derived from *Aeropyrum pernix* and *Mycobacterium tuberculosis* H37Rv, which were previously reported (Mino K and Ishikawa K, FEBS letters, 551: 133-138, 2003; Westrop G D, Goodall G, Mottram J C and Coombs G H, J. Biol. Chem., 281: 25062-25075, 2006), were confirmed to have the activity of using OPS as a substrate to synthesize cysteine. The cysteine synthesis activity of the novel *Mycobacterium smegmatis* str. MC2 155-derived OPS sulfhydrylase, which was obtained by screening amino acid homology with the Mtb-OPSS enzyme, was first found.

As seen in the data of Table 12, the conversion rate from OPS into cysteine of Ape-OPSS reached near 100% in one hour. The final conversion rate of the Msm-OPSS enzyme, which was newly selected through enzyme screening on the basis of previously reported *Mycobacterium tuberculosis* H37Rv-derived OPSS, was 43.7% that was 4.3 times as high as that of Mtb-OPSS. On the other hand, the novel *Nocardia farcinica* IFM 10152-derived OPS sulfhydrylase, obtained by the homology screening, exhibited insufficient activity of converting O-phosphoserine into cysteine.

Example 12

Preparation of Mtb-T and Msm-T that Encode C-Terminally 5 Amino Acid Residues truncated Mtb-OPSS and Msm-OPSS

*Mycobacterium tuberculosis* H37Rv-derived OPSS (Mtb-OPSS), which catalyzes the conversion of OPS to cysteine with the aid of the additional enzymes mec+ and cysO, is reported to be able to use an $S^{2-}$ containing sulfur source in converting OPS to cysteine even in the absence of the additional enzymes when five C-terminal amino acid residues are removed therefrom (Agren D, Schnell R and Schneider G, FEBS letters, 583: 330-336, 2009). On the basis of this report, Mtb-T (SEQ ID NO: 11), which can rapidly convert OPS in the presence of $S^{2-}$ as a sulfur source, was obtained. Msm-T was also obtained from Msm-OPSS (SEQ ID NO: 9) that shares an amino acid homology with Mtb-OPSS. Expression vectors carrying the two enzyme mutants were constructed. In this regard, pfu PCR was performed on the genomic DNA of *Mycobacterium tuberculosis* H37Rv or *Mycobacterium smegmatis* in the presence of a pair of primers of SEQ ID NOS: 63, 64, 65 and 66. The OPSS gene fragments thus obtained were treated with NdeI and HindIII and were cloned into the pET28a vector digested with the same restriction enzymes to construct recombinant expression vectors named pET28a-Mtb-T and pET28a-Msm-T, respectively. The recombinant expression vectors were introduced into *E. coli* (DE3). The expression of the two mutant OPSS enzymes was confirmed by 14% SDS PAGE. The two mutant OPSS enzymes are purified and expressed in the same conditions as in Example 10. As a result, Mtb-T (SEQ ID NO: 11) and Msm-T (SEQ ID NO: 10) were obtained.

Example 13

Assay of Mtb-T and Msm-T for Cysteine Conversion Activity

On the basis of the report that *Mycobacterium tuberculosis* H37Rv-derived OPSS mutants devoid of five C-terminal amino acid residues show increased affinity for an $S^{2-}$ group-containing sulfur source even in the absence of subsidiary enzymes (Agren D, Schnell R and Schneider G, FEBS letters, 583: 330-336, 2009), Mtb-T and Msm-T were obtained. They were evaluated for enzymatic activity by measuring final cysteine conversion rates. Enzymatic activity was assayed in the same condition and manner as in Example 11. The produced cysteine was quantitatively analyzed using the Gaitonde method.

TABLE 13

|  | Cysteine Conversion Rate (%) | | |
| --- | --- | --- | --- |
|  | 10 min | 30 min | 60 min |
| Mtb-T | 9.5 | 18.6 | 37.1 |
| Msm-T | 20.3 | 54.6 | 100 |

As seen in Table 13, Msm-T, being devoid of the five C-terminal amino acid residues of *Mycobacterium smegmatis* str. MC2 155-derived OPSS allowed the conversion of cysteine from the substrate at a rate of 100% in one hour.

When its amino acid sequence was modified, the O-phosphoserine sulfhydrylase (OPSS) can more effectively catalyze the biosynthesis of L-cysteine.

Example 14

Requirement of Cofactor for OPS Sulfhydrylase Activity

To examine the effect of cofactors on the cysteine conversion of OPSS, the cysteine conversion rate of Msm-T was measured in the absence or presence of PLP (pyridoxal-5'-phosphate) and DTT (dithiothreitol). In this regard, the substrates of 50 mM OPS broth and 100 mM $Na_2S$ were reacted at 37° C. for 30 min in the presence of 25 mM DTT or 0.2 mM PLP. The cysteine thus produced was quantitatively analyzed using the Gaitonde method. As seen in Table 14, the cysteine conversion rate in the presence of both PLP and DTT was 2.3 times as large as that in the absence of both PLP and DTT. Thus, both PLP and DTT were observed to have a positive influence on the conversion.

TABLE 14

| Msm-T | Cysteine Conversion Rate (%) |
| --- | --- |
| (−) PLP, (−) DTT | 23.62 |
| (+) PLP, (−) DTT | 33.21 |
| (−) PLP, (+) DTT | 40.08 |
| (+) PLP, (+) DTT | 54.65 |

Example 15

The Influence of Temperature on the Activity of OPS Sulfhydrylase

Figure 2:
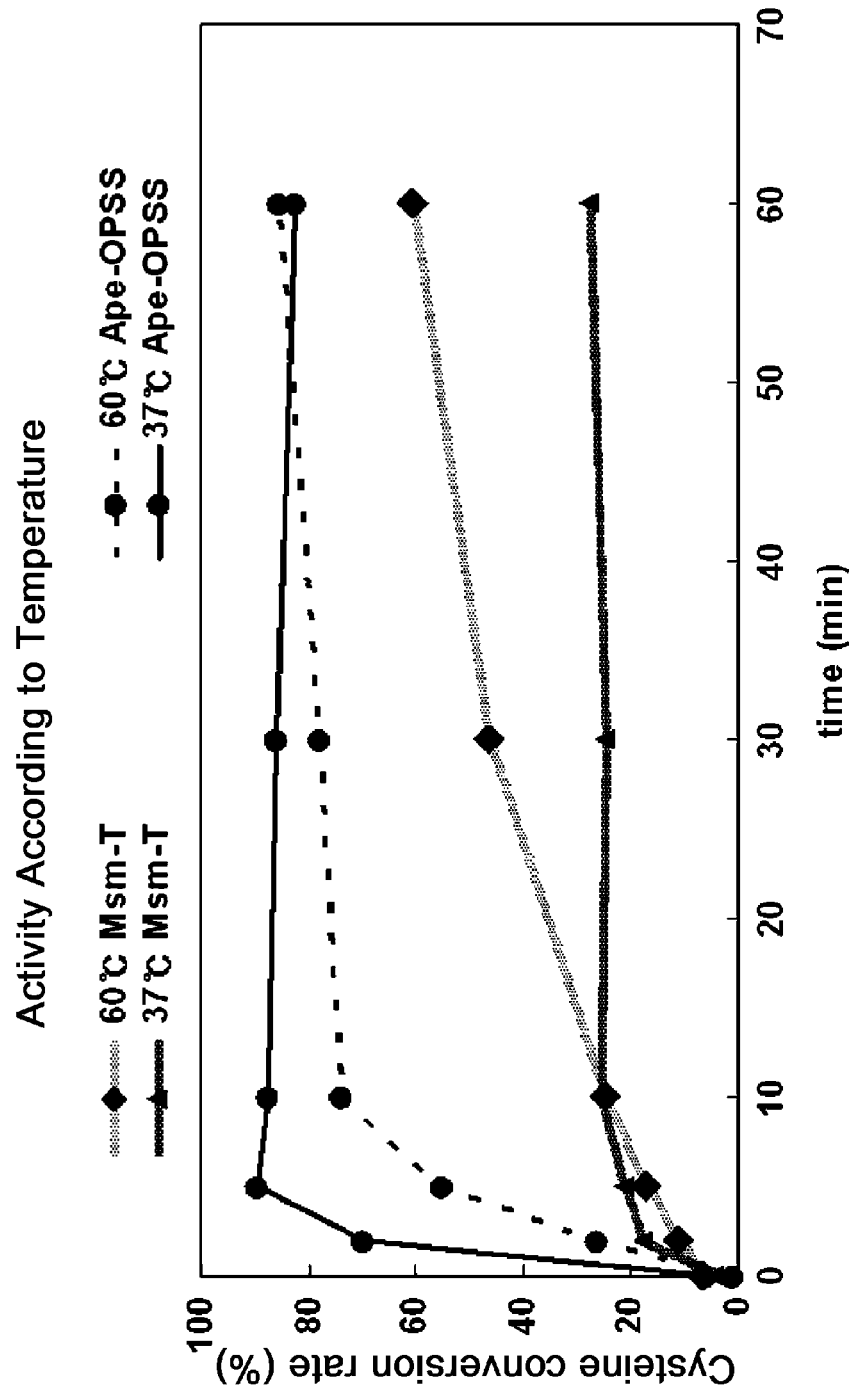
FIG. 2 is a graph showing the activity of OPS sulfhydrylase according to temperatures.

The cysteine conversion rates of Ape-OPSS and Msm-T according to temperatures were examined. The enzymatic activity at 37° C. and 60° C. was measured 2, 5, 10, 30, and 60 min after reaction. The reaction was conducted under the condition of 100 mM HEPES (pH 7.4), 5 mM OPS, 10 mM $Na_2S$, 0.2 mM PLP, and CysM 50 μg/mL. The amount of produced cysteine was determined using the Gaitonde method. In the condition of a buffer, as shown in FIG. 2, Ape-OPSS showed a faster initial reaction rate at 37° C. as well as higher reactivity at 60° C. than did Msm-T.

Example 16

Heat Stability of OPS Sulfhydrylase

Ape-OPSS and Msm-T were analyzed for heat stability. Each of the enzymes was diluted to a concentration of 2 mg/mL in an OPS broth and thermally treated at 37° C. and 60° C. for 10, 30, 60, 120, and 240 min, followed by reaction at 37° C. for 30 min under the condition of 5 mM OPS, 10 mM Na$_2$S, 0.2 mM PLP, and 100 mM HEPES (pH 7.4). For this reaction, 10 μg/mL Ape-OPSS and 50 μg/mL Msm-T were employed. The amounts of the produced cysteine were measured using the Gaitonde method. Ape-OPSS was observed to retain its intact activity in spite of heat treatment at 60° C. for 4 hours while the activity of Msm-T was maintained at 37° C., but decreased by 50% upon heat treatment at 60° C. for 30 min. The results are given in Table 15, below.

TABLE 15

| | Relative activity (%) Heating time (min) | | | | | |
|---|---|---|---|---|---|---|
| | (—) | 10 min | 30 min | 60 min | 120 min | 240 min |
| Ape-OPSS | 100 | 102 | 107 | 100 | 107 | 101 |
| Msm-T | 100 | 82 | 50 | 32 | 19 | 8 |

An examination was made of the retention of enzymatic activity at 37° C. when Msm-T was used in an amount of 50 μg/mL, which is a practical concentration in OPS broth. In the absence of Na$_2$S, 50 μg/mL Msm-T was treated, together with 50 mM OPS broth and 0.2 mM PLP, at 37° C. for 0.5, 1, 2, 4, and 6 hours, after which Na$_2$S was added to induce the enzymatic reaction. After the reaction for 30 min, the activity of Msm-T was measured. The amounts of the produced cysteine were determined using the Gaitonde method. As a result, the activity of Msm-T was decreased below 50% 2 hours after reaction at 37° C. in OPS broth (Table 16).

TABLE 16

| Time | 0 | 30 min | 60 min | 120 min | 240 min | 360 min |
|---|---|---|---|---|---|---|
| Cysteine conversion rate (%) | 100 | 88 | 73 | 47 | 11 | 3 |

Example 17

The Influence of pH on the OPS Sulfhydrylase

Figure 3:
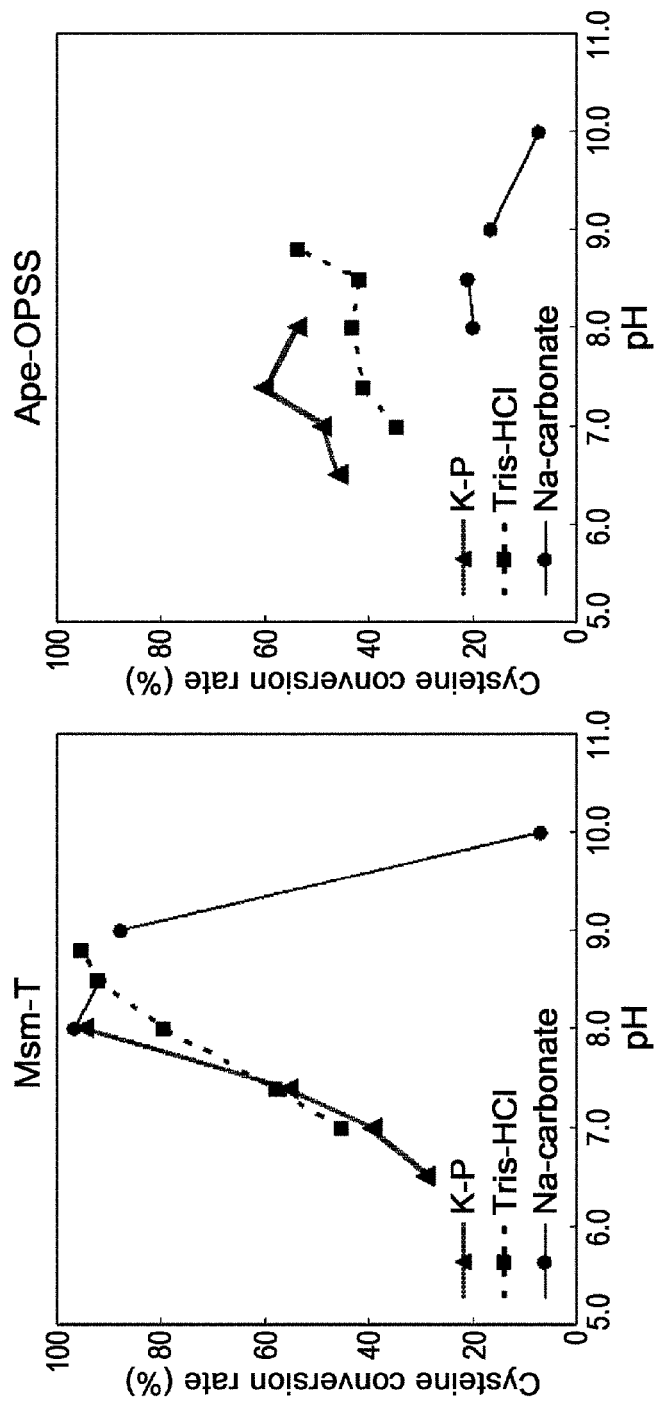
FIG. 3 is a set of graphs showing pH sensitivity of OPS sulfhydrylase.

The cysteine conversion rates of Ape-OPSS and Msm-T according to pH were measured. In 100 mM buffer, Ape-OPSS and Msm-T, each having a concentration of 50 μg/mL, were subjected to reaction at 37° C. for 10 min. In this regard, K-phosphate buffer with a pH of 6.4/7.0/7.4/8.0, Tris-HCl buffer with a pH of 7.0/7.4/8.0/8.5/8.8, and Na-carbonate buffer with a pH of 8.0/8.5/9.0/10.0 were used. The quantitative analysis of the produced cysteine was conducted using the Gaitonde method. As seen in FIG. 3, Msm-T exhibited the highest activity at a pH of from 8.0 to 9.0 irrespective of buffer. As for Ape-OPSS, its highest activity was detected in K-phosphate (pH 7.4), with an optimal pH differing from one buffer to another.

Example 18

Effect of Ions on the Activity of OPS Sulfhydrylase

Effects of ions on the activity of the OPSS enzymes were examined as follows. In a reaction mixture containing 5 mM OPS, 10 mM Na$_2$S, 0.2 mM PLP, and 100 mM HEPES (pH 7.4), the enzymes were subjected to reaction at 37° C. for 30 min in the presence of (NH$_4$)$_2$SO$_4$ (1, 3, 5, 10, 20 g/L), KH$_2$PO$_4$ (0.5, 1, 2, 4, 8 g/L), or NH$_4$Cl (0.2, 0.5, 1, 2 g/L). Ape-OPSS and Msm-T were used at a concentration of 10 μg/mL and 50 μg/mL, respectively. The amounts of the produced cysteine were determined using the Gaitonde method.

No changes were detected in the cysteine conversion rate when (NH$_4$)$_2$SO$_4$ or KH$_2$PO$_4$ was added to the reaction mixture. On the other hand, as seen in Table 17, the cysteine conversion rate was decreased with an increase in NH$_4$Cl concentration. Particularly, the maximal enzyme activity was decreased by more than 70% when 2 g/L NH$_4$Cl was added. Therefore, NH$_4$Cl was observed to have a negative effect on the conversion activity of OPS sulfhydrylase.

TABLE 17

| | Relative activity (%) | |
|---|---|---|
| NH$_4$Cl | Ape-OPSS | Msm-T |
| 0 | 100.00 | 100.00 |
| 0.2 | 86.26 | 91.49 |
| 0.5 | 73.35 | 91.30 |
| 1 | 49.11 | 67.11 |
| 2 | 27.72 | 47.12 |

Example 19

Effect of Sulfur Source on the Cysteine Synthesis Activity of OPS Sulfhydrylase

An experiment was conducted to examine the effect of sulfur sources on the cysteine synthesis activity of each enzyme. In a reaction mixture containing 5 mM OPS, 0.2 mM PLP, and 100 mM HEPES, each enzyme (50 μg/mL Ape-OPSS, 50 μg/mL Msm-T) was subjected to reaction at 37° C. for 1 hour in the presence of 10 mM Na$_2$S, NaSH, or Na$_2$S$_2$O$_3$. The amounts of the produced cysteine were measured using the Gaitonde method. Ape-OPSS was observed to prefer Na$_2$S$_2$O$_3$ as a sulfur source, whereas Msm-T prefers Na$_2$S. The results are summarized in Table 18, below.

TABLE 18

| | Relative activity (%) | | |
|---|---|---|---|
| Enzyme | Na$_2$S | NaSH | Na$_2$S$_2$O$_3$ |
| Ape-OPSS | 100.0 | 95.2 | 142.3 |
| Msm-T | 106.7 | 98.3 | 66.2 |

Example 20

Figure 4:
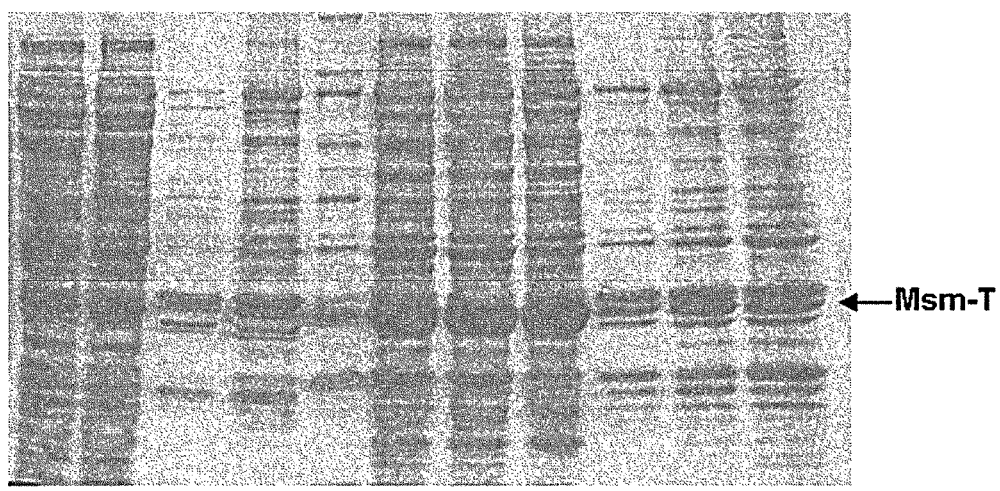
FIG. 4 is a photograph showing the expression level of Msm-T in a pET system and a pCL-Pcj1 system as analyzed by SDS PAGE.

Construction of the Expression Vector Carrying OPS Sulfhydrylase (pCL-Pcj1 System) and Expression in E. coli PCR was performed using primers of SEQ ID NOS: 67 and 68, with the pET28a-Msm-T vector serving as a template. The PCR product thus obtained was treated with EcoRV and HindIII and cloned into pCL-P(CJ1) to construct a recombinant vector named pCL-P(CJ1)-Msm-T. To examine a difference in the expression level of Msm-T between the pET system and the pCL-Pcj1 system, strains for expressing the enzyme were prepared. The pET system was introduced into Rosetta (DE3) while the pCL-Pcj1 system used the K12G strain. Single colonies taken from LB plates were inoculated into 5 mL of LB broth and cultured at 37° C. for 16 hours while shaking at 200 rpm. These cultures were transferred to 25 mL of fresh LB broth containing kanamycine or spectinomycine and 0.2% glucose (in 250 mL flasks) and incubated to an $OD_{600}$ of 0.5-0.6, immediately after which 1 mM IPTG was added to the media to induce the enzymes to be expressed. During incubation at 37° C. while shaking at 200 rpm, the expression levels of the enzyme were measured at various culture times (8, 16, 24 hours). The enzyme expression levels of the two systems were analyzed on 14% SDS PAGE (FIG. 4).

Example 21

Cysteine Synthesis by OPS Sulfhydrylase with the Purified OPS Fermentation Broth The conversion rates from purified OPS to cysteine of Msm-T and Ape-OPSS were determined. In the presence of 75 μg/mL of each of the enzymes and 0.2 mM PLP, 60 mM OPS purified from OPS fermentation broth was reacted with 120 mM $Na_2S$ at 37° C. or 70° C. for 30, 60, 90, and 120 min. The reaction was conducted only at 37° C. for Msm-T, but at both 37° C. and 70° C. for Ape-OPSS. The amounts of the produced cysteine were measured using the Gaitonde method. As seen in FIG. 5, a purified OPS fermentation broth served well as a substrate for the enzymatic conversion into cysteine. Particularly, the conversion rate of Ape-OPSS was increased at 70° C. even upon the use of the purified OPS fermentation broth.

Example 22

Cysteine Synthesis by OPS Sulfhydrylase with the OPS Fermentation Broth

When an OPS fermentation broth was used as a substrate, the cysteine conversion rates of Msm-T and Ape-OPSS were measured according to the concentrations of the enzymes. In the presence of 100 mM $Na_2S$ and 0.2 mM PLP, 50 mM of OPS fermentation broth was reacted with 5 μg/mL or 50 μg/mL of each of Msm-T and Ape-OPSS at 37° C. The amounts of the produced cysteine were measured using the Gaitonde method. As seen in FIG. 6, the highest conversion rate was detected in 50 μg/mL Msm-T. In addition, upon the use of OPS fermentation broth as a substrate, the activity of Msm-T was higher than that of Ape-OPSS.

Example 23

Cysteine Conversion Rate According to OPS Concentration

To examine the effect of OPS concentration on the conversion rate of Msm-T, predetermined amounts of purified OPS were added to OPS fermentation broth to induce the conversion reaction. The enzyme was used in an amount of 50 μg. The amounts of cysteine in the reaction solution were measured using the Gaitonde method. Msm-T exhibited a conversion rate of as high as 100% when the concentration of OPS was about 30 g/L.

When the concentration of OPS exceeded 50 g/L, both the conversion rate and the conversion percentage were found to decrease. From these results, it is understood that when OPS fermentation broth is used as a substrate, there is an optimal concentration ratio between OPS and the enzyme.

TABLE 19

| Cysteine Conversion Rate (Msm-T 50 ug) | | | | | | |
|---|---|---|---|---|---|---|
| Time | 0 min | 10 min | 30 min | 60 min | 120 min | 180 min |
| OPS measured 10.65 g/l | 0 | 23.03 | 65.38 | 65.70 | 61.95 | 55.35 |
| OPS measured 36.09 g/l | 0 | 1.15 | 10.23 | 28.07 | 97.84 | 100.34 |
| OPS measured 55.6 g/l | 0 | 0 | 2.36 | 7.41 | 42.69 | 66.67 |

The invention claimed is:

1. A method for producing cysteine or a derivative thereof, comprising:
   1) culturing a recombinant microorganism in which the activity of endogeneous phosphoserine phosphatase (SerB) is reduced and the activity of phosphoglycerate dehydrogenase (SerA) is enhanced, to produce O-sphosphoserine (OPS) wherein the SerA has one selected from the group consisting of amino acid sequences of SEQ ID NOS: 3 to 7; and
   2) reacting the OPS of step 1) with a sulfide in presence of O-phosphoserine sulfhydrylase (OPSS) or a microorganism expressing OPSS, to produce cysteine or a derivative thereof.

2. The method of claim 1, wherein the phosphoserine phosphatase has an amino acid sequence of SEQ ID NO: 2.

3. The method of claim 1, wherein the level of enzyme activity is reduced by using a technique selected from the group consisting of deletion of the chromosomal serB, the introduction of mutation into the chromosomal serB to reduce endogenouse SerB activity, the substitution of the chromosomal serB with a gene mutated to reduce the endogenouse SerB activity, the introduction of mutation into a regulatory region for the serB to reduce endogenouse SerB activity, and the introduction of an antisense oligonucleotide complementary to a transcript of the serB to inhibit the translation of the mRNA.

4. The method of claim 3, wherein the recombinant microorganism in which the activity of endogenous SerB is disrupted is cultured in a medium containing glycine or serine.

5. The method of claim 4, wherein the medium contains glycine in an amount of from 0.1 to 10 g/L.

6. The method of claim 4, wherein the medium contains serine in an amount of from 0.1 to 5 g/L.

7. The method of claim 1, wherein the SerA is a wild-type or a mutant resistant to serine feedback inhibition.

8. The method of claim 1, wherein the level of enzyme activity is enhanced by using a technique selected from the group consisting of increasing a copy number of a gene encoding the enzyme, introducing a mutation into a regulatory region for the gene to enhance the enzyme activity, substituting the chromosomal gene with a gene mutated to enhance the enzyme, and introducing a mutation into the chromosomal gene to enhance the enzyme activity.

9. The method of claim 1, wherein the recombinant microorganism is *Escherichia* sp, or *Coryneform* bacteria.

10. The method of claim 1, wherein the sulfide of step 2) is selected from the group consisting of $Na_2S$, NaSH, $(NH_4)_2S$, $H_2S$, $Na_2S_2O_3$ and a combination thereof.

11. The method of claim 1, wherein the sulfide of step 2) is used at a molar concentration 0.1 to 3 times as high as that of OPS used in the enzymatic conversion.

12. The method of claim 1, wherein the OPSS of step 2) is derived from at least one species selected from the group consisting of *Aeropyrum pernix, Mycobacterium tuberculosis, Mycobacterium smegmatis* and *Trichomonas vaginalis*.

13. The method of claim 12, wherein the OPSS is a further modified to increase a conversion rate of step 2).

14. The method of claim 1, wherein the conversion of step 2) is carried out in presence of a cofactor selected from 0.001~2 mM PLP (pyridoxal-5-phosphate), 0.001~100 mM DTT (dithiothreitol), and a combination thereof.

15. The method of claim 1, further comprising isolating and purifying the cysteine or its derivatives.

16. The method of claim 1, wherein the recombinant microorganism of step 1) further has enhanced activity of the phosphoserine aminotransferase (SerC).

17. The method of claim 16, wherein:
the SerC has an amino acid sequence of SEQ ID NO: 8.

* * * * *

SEQUENCE LISTING

```
<160> NUMBER OF SEQ ID NOS: 68

<210> SEQ ID NO 1
<211> LENGTH: 446
<212> TYPE: PRT
<213> ORGANISM: Corynebacterium glutamicum 13032
<220> FEATURE:
<221> NAME/KEY: PEPTIDE
<222> LOCATION: (1)..(446)
<223> OTHER INFORMATION: phosphoserine phosphatase, SerB

<400> SEQUENCE: 1

Met Ser Cys Ser Ala Leu Arg His Glu Thr Ile Val Ala Val Thr Glu
 1               5                  10                  15

Leu Ile Gln Asn Glu Ser Gln Glu Ile Ala Glu Leu Glu Ala Gly Gln
            20                  25                  30

Gln Val Ala Leu Arg Glu Gly Tyr Leu Pro Ala Val Ile Thr Val Ser
        35                  40                  45

Gly Lys Asp Arg Pro Gly Val Thr Ala Ala Phe Phe Arg Val Leu Ser
    50                  55                  60

Ala Asn Gln Val Gln Val Leu Asp Val Glu Gln Ser Met Phe Arg Gly
65                  70                  75                  80
```

```
Phe Leu Asn Leu Ala Ala Phe Val Gly Ile Ala Pro Glu Arg Val Glu
                 85                  90                  95

Thr Val Thr Thr Gly Leu Thr Asp Thr Leu Lys Val His Gly Gln Ser
            100                 105                 110

Val Val Val Glu Leu Gln Glu Thr Val Gln Ser Ser Arg Pro Arg Ser
            115                 120                 125

Ser His Val Val Val Leu Gly Asp Pro Val Asp Ala Leu Asp Ile
            130                 135                 140

Ser Arg Ile Gly Gln Thr Leu Ala Asp Tyr Asp Ala Asn Ile Asp Thr
145                 150                 155                 160

Ile Arg Gly Ile Ser Asp Tyr Pro Val Thr Gly Leu Glu Leu Lys Val
                165                 170                 175

Thr Val Pro Asp Val Ser Pro Gly Gly Gly Glu Ala Met Arg Lys Ala
            180                 185                 190

Leu Ala Ala Leu Thr Ser Glu Leu Asn Val Asp Ile Ala Ile Glu Arg
            195                 200                 205

Ser Gly Leu Leu Arg Arg Ser Lys Arg Leu Val Cys Phe Asp Cys Asp
    210                 215                 220

Ser Thr Leu Ile Thr Gly Glu Val Ile Glu Met Leu Ala Ala His Ala
225                 230                 235                 240

Gly Lys Glu Ala Glu Val Ala Ala Val Thr Glu Arg Ala Met Arg Gly
                245                 250                 255

Glu Leu Asp Phe Glu Glu Ser Leu Arg Glu Arg Val Lys Ala Leu Ala
            260                 265                 270

Gly Leu Asp Ala Ser Val Ile Asp Glu Val Ala Ala Ile Glu Leu
            275                 280                 285

Thr Pro Gly Ala Arg Thr Thr Ile Arg Thr Leu Asn Arg Met Gly Tyr
290                 295                 300

Gln Thr Ala Val Val Ser Gly Gly Phe Ile Gln Val Leu Glu Gly Leu
305                 310                 315                 320

Ala Glu Glu Leu Glu Leu Asp Tyr Val Arg Ala Asn Thr Leu Glu Ile
                325                 330                 335

Val Asp Gly Lys Leu Thr Gly Asn Val Thr Gly Lys Ile Val Asp Arg
            340                 345                 350

Ala Ala Lys Ala Glu Phe Leu Arg Glu Phe Ala Ala Asp Ser Gly Leu
            355                 360                 365

Lys Met Tyr Gln Thr Val Ala Val Gly Asp Gly Ala Asn Asp Ile Asp
370                 375                 380

Met Leu Ser Ala Ala Gly Leu Gly Val Ala Phe Asn Ala Lys Pro Ala
385                 390                 395                 400

Leu Lys Glu Ile Ala Asp Thr Ser Val Asn His Pro Phe Leu Asp Glu
                405                 410                 415

Val Leu His Ile Met Gly Ile Ser Arg Asp Gly Ile Asp Leu Ala Asp
            420                 425                 430

Gln Glu Asp Gly Thr Phe His Arg Val Pro Leu Thr Asn Ala
            435                 440                 445

<210> SEQ ID NO 2
<211> LENGTH: 322
<212> TYPE: PRT
<213> ORGANISM: Escherichia coli K12 W3110
<220> FEATURE:
<221> NAME/KEY: PEPTIDE
<222> LOCATION: (1)..(322)
<223> OTHER INFORMATION: phosphoserine phosphatase, SerB

<400> SEQUENCE: 2
```

```
Met Pro Asn Ile Thr Trp Cys Asp Leu Pro Glu Asp Val Ser Leu Trp
 1               5                  10                  15
Pro Gly Leu Pro Leu Ser Leu Ser Gly Asp Glu Val Met Pro Leu Asp
            20                  25                  30
Tyr His Ala Gly Arg Ser Gly Trp Leu Tyr Gly Arg Gly Leu Asp
            35                  40                  45
Lys Gln Arg Leu Thr Gln Tyr Gln Ser Lys Leu Gly Ala Ala Met Val
        50                  55                  60
Ile Val Ala Ala Trp Cys Val Glu Asp Tyr Gln Val Ile Arg Leu Ala
 65                  70                  75                  80
Gly Ser Leu Thr Ala Arg Ala Thr Arg Leu Ala His Glu Ala Gln Leu
                85                  90                  95
Asp Val Ala Pro Leu Gly Lys Ile Pro His Leu Arg Thr Pro Gly Leu
            100                 105                 110
Leu Val Met Asp Met Asp Ser Thr Ala Ile Gln Ile Glu Cys Ile Asp
            115                 120                 125
Glu Ile Ala Lys Leu Ala Gly Thr Gly Glu Met Val Ala Glu Val Thr
130                 135                 140
Glu Arg Ala Met Arg Gly Glu Leu Asp Phe Thr Ala Ser Leu Arg Ser
145                 150                 155                 160
Arg Val Ala Thr Leu Lys Gly Ala Asp Ala Asn Ile Leu Gln Gln Val
                165                 170                 175
Arg Glu Asn Leu Pro Leu Met Pro Gly Leu Thr Gln Leu Val Leu Lys
            180                 185                 190
Leu Glu Thr Leu Gly Trp Lys Val Ala Ile Ala Ser Gly Gly Phe Thr
            195                 200                 205
Phe Phe Ala Glu Tyr Leu Arg Asp Lys Leu Arg Leu Thr Ala Val Val
        210                 215                 220
Ala Asn Glu Leu Glu Ile Met Asp Gly Lys Phe Thr Gly Asn Val Ile
225                 230                 235                 240
Gly Asp Ile Val Asp Ala Gln Tyr Lys Ala Lys Thr Leu Thr Arg Leu
                245                 250                 255
Ala Gln Glu Tyr Glu Ile Pro Leu Ala Gln Thr Val Ala Ile Gly Asp
            260                 265                 270
Gly Ala Asn Asp Leu Pro Met Ile Lys Ala Ala Gly Leu Gly Ile Ala
            275                 280                 285
Tyr His Ala Lys Pro Lys Val Asn Glu Lys Ala Glu Val Thr Ile Arg
        290                 295                 300
His Ala Asp Leu Met Gly Val Phe Cys Ile Leu Ser Gly Ser Leu Asn
305                 310                 315                 320
Gln Lys

<210> SEQ ID NO 3
<211> LENGTH: 530
<212> TYPE: PRT
<213> ORGANISM: Artificial Sequence
<220> FEATURE:
<223> OTHER INFORMATION: D-3-phosphoglycerate dehydrogenase(E235K),
      SerA(E235K)

<400> SEQUENCE: 3

Met Ser Gln Asn Gly Arg Pro Val Val Leu Ile Ala Asp Lys Leu Ala
 1               5                  10                  15
Gln Ser Thr Val Asp Ala Leu Gly Asp Ala Val Glu Val Arg Trp Val
            20                  25                  30
```

```
Asp Gly Pro Asn Arg Pro Glu Leu Leu Asp Ala Val Lys Glu Ala Asp
         35                  40                  45
Ala Leu Leu Val Arg Ser Ala Thr Thr Val Asp Ala Glu Val Ile Ala
 50                  55                  60
Ala Ala Pro Asn Leu Lys Ile Val Gly Arg Ala Gly Val Gly Leu Asp
 65                  70                  75                  80
Asn Val Asp Ile Pro Ala Ala Thr Glu Ala Gly Val Met Val Ala Asn
                 85                  90                  95
Ala Pro Thr Ser Asn Ile His Ser Ala Cys Glu His Ala Ile Ser Leu
             100                 105                 110
Leu Leu Ser Thr Ala Arg Gln Ile Pro Ala Ala Asp Ala Thr Leu Arg
         115                 120                 125
Glu Gly Glu Trp Lys Arg Ser Ser Phe Asn Gly Val Glu Ile Phe Gly
         130                 135                 140
Lys Thr Val Gly Ile Val Gly Phe Gly His Ile Gly Gln Leu Phe Ala
145                 150                 155                 160
Gln Arg Leu Ala Ala Phe Glu Thr Thr Ile Val Ala Tyr Asp Pro Tyr
                 165                 170                 175
Ala Asn Pro Ala Arg Ala Ala Gln Leu Asn Val Glu Leu Val Glu Leu
             180                 185                 190
Asp Glu Leu Met Ser Arg Ser Asp Phe Val Thr Ile His Leu Pro Lys
         195                 200                 205
Thr Lys Glu Thr Ala Gly Met Phe Asp Ala Gln Leu Leu Ala Lys Ser
         210                 215                 220
Lys Lys Gly Gln Ile Ile Ile Asn Ala Ala Arg Gly Gly Leu Val Asp
225                 230                 235                 240
Glu Gln Ala Leu Ala Asp Ala Ile Glu Ser Gly His Ile Arg Gly Ala
                 245                 250                 255
Gly Phe Asp Val Tyr Ser Thr Glu Pro Cys Thr Asp Ser Pro Leu Phe
             260                 265                 270
Lys Leu Pro Gln Val Val Val Thr Pro His Leu Gly Ala Ser Thr Glu
         275                 280                 285
Glu Ala Gln Asp Arg Ala Gly Thr Asp Val Ala Asp Ser Val Leu Lys
         290                 295                 300
Ala Leu Ala Gly Glu Phe Val Ala Asp Ala Val Asn Val Ser Gly Gly
305                 310                 315                 320
Arg Val Gly Glu Lys Val Ala Val Trp Met Asp Leu Ala Arg Lys Leu
                 325                 330                 335
Gly Leu Leu Ala Gly Lys Leu Val Asp Ala Ala Pro Val Ser Ile Glu
             340                 345                 350
Val Glu Ala Arg Gly Glu Leu Ser Ser Glu Gln Val Asp Ala Leu Gly
         355                 360                 365
Leu Ser Ala Val Arg Gly Leu Phe Ser Gly Ile Ile Glu Glu Ser Val
         370                 375                 380
Thr Phe Val Asn Ala Pro Arg Ile Ala Glu Glu Arg Gly Leu Asp Ile
385                 390                 395                 400
Ser Val Lys Thr Asn Ser Glu Ser Val Thr His Arg Ser Val Leu Gln
                 405                 410                 415
Val Lys Val Ile Thr Gly Ser Gly Ala Ser Ala Thr Val Val Gly Ala
             420                 425                 430
Leu Thr Gly Leu Glu Arg Val Glu Lys Ile Thr Arg Ile Asn Gly Arg
         435                 440                 445
Gly Leu Asp Leu Arg Ala Glu Gly Leu Asn Leu Phe Leu Gln Tyr Thr
         450                 455                 460
```

```
Asp Ala Pro Gly Ala Leu Gly Thr Val Gly Thr Lys Leu Gly Ala Ala
465                 470                 475                 480

Gly Ile Asn Ile Glu Ala Ala Leu Thr Gln Ala Glu Lys Gly Asp
            485                 490                 495

Gly Ala Val Leu Ile Leu Arg Val Glu Ser Ala Val Ser Glu Leu
        500                 505                 510

Glu Ala Glu Ile Asn Ala Glu Leu Gly Ala Thr Ser Phe Gln Val Asp
        515                 520                 525

Leu Asp
    530

<210> SEQ ID NO 4
<211> LENGTH: 333
<212> TYPE: PRT
<213> ORGANISM: Artificial Sequence
<220> FEATURE:
<223> OTHER INFORMATION: D-3-phosphoglycerate dehydrogenase(197 delta),
      SerA(197 delta)

<400> SEQUENCE: 4

Met Ser Gln Asn Gly Arg Pro Val Val Leu Ile Ala Asp Lys Leu Ala
1               5                   10                  15

Gln Ser Thr Val Asp Ala Leu Gly Asp Ala Val Glu Val Arg Trp Val
            20                  25                  30

Asp Gly Pro Asn Arg Pro Glu Leu Leu Asp Ala Val Lys Glu Ala Asp
        35                  40                  45

Ala Leu Leu Val Arg Ser Ala Thr Thr Val Asp Ala Glu Val Ile Ala
    50                  55                  60

Ala Ala Pro Asn Leu Lys Ile Val Gly Arg Ala Gly Val Gly Leu Asp
65                  70                  75                  80

Asn Val Asp Ile Pro Ala Ala Thr Glu Ala Gly Val Met Val Ala Asn
                85                  90                  95

Ala Pro Thr Ser Asn Ile His Ser Ala Cys Glu His Ala Ile Ser Leu
            100                 105                 110

Leu Leu Ser Thr Ala Arg Gln Ile Pro Ala Ala Asp Ala Thr Leu Arg
        115                 120                 125

Glu Gly Glu Trp Lys Arg Ser Ser Phe Asn Gly Val Glu Ile Phe Gly
    130                 135                 140

Lys Thr Val Gly Ile Val Gly Phe Gly His Ile Gly Gln Leu Phe Ala
145                 150                 155                 160

Gln Arg Leu Ala Ala Phe Glu Thr Thr Ile Val Ala Tyr Asp Pro Tyr
                165                 170                 175

Ala Asn Pro Ala Arg Ala Ala Gln Leu Asn Val Glu Leu Val Glu Leu
            180                 185                 190

Asp Glu Leu Met Ser Arg Ser Asp Phe Val Thr Ile His Leu Pro Lys
        195                 200                 205

Thr Lys Glu Thr Ala Gly Met Phe Asp Ala Gln Leu Leu Ala Lys Ser
    210                 215                 220

Lys Lys Gly Gln Ile Ile Ile Asn Ala Ala Arg Gly Gly Leu Val Asp
225                 230                 235                 240

Glu Gln Ala Leu Ala Asp Ala Ile Glu Ser Gly His Ile Arg Gly Ala
                245                 250                 255

Gly Phe Asp Val Tyr Ser Thr Glu Pro Cys Thr Asp Ser Pro Leu Phe
            260                 265                 270

Lys Leu Pro Gln Val Val Val Thr Pro His Leu Gly Ala Ser Thr Glu
        275                 280                 285
```

```
Glu Ala Gln Asp Arg Ala Gly Thr Asp Val Ala Asp Ser Val Leu Lys
    290                 295                 300

Ala Leu Ala Gly Glu Phe Val Ala Asp Ala Val Asn Val Ser Gly Gly
305                 310                 315                 320

Arg Val Gly Glu Glu Val Ala Val Trp Met Asp Leu Ala
                325                 330

<210> SEQ ID NO 5
<211> LENGTH: 410
<212> TYPE: PRT
<213> ORGANISM: Artificial Sequence
<220> FEATURE:
<223> OTHER INFORMATION: D-3-phosphoglycerate dehydrogenase(G336V),
      SerA(G336V)

<400> SEQUENCE: 5

Met Ala Lys Val Ser Leu Glu Lys Asp Lys Ile Lys Phe Leu Leu Val
1               5                   10                  15

Glu Gly Val His Gln Lys Ala Leu Glu Ser Leu Arg Ala Ala Gly Tyr
                20                  25                  30

Thr Asn Ile Glu Phe His Lys Gly Ala Leu Asp Asp Glu Gln Leu Lys
            35                  40                  45

Glu Ser Ile Arg Asp Ala His Phe Ile Gly Leu Arg Ser Arg Thr His
        50                  55                  60

Leu Thr Glu Asp Val Ile Asn Ala Ala Glu Lys Leu Val Ala Ile Gly
65                  70                  75                  80

Cys Phe Cys Ile Gly Thr Asn Gln Val Asp Leu Asp Ala Ala Ala Lys
                85                  90                  95

Arg Gly Ile Pro Val Phe Asn Ala Pro Phe Ser Asn Thr Arg Ser Val
                100                 105                 110

Ala Glu Leu Val Ile Gly Glu Leu Leu Leu Leu Leu Arg Gly Val Pro
            115                 120                 125

Glu Ala Asn Ala Lys Ala His Arg Gly Val Trp Asn Lys Leu Ala Ala
        130                 135                 140

Gly Ser Phe Glu Ala Arg Gly Lys Lys Leu Gly Ile Ile Gly Tyr Gly
145                 150                 155                 160

His Ile Gly Thr Gln Leu Gly Ile Leu Ala Glu Ser Leu Gly Met Tyr
                165                 170                 175

Val Tyr Phe Tyr Asp Ile Glu Asn Lys Leu Pro Leu Gly Asn Ala Thr
                180                 185                 190

Gln Val Gln His Leu Ser Asp Leu Leu Asn Met Ser Asp Val Val Ser
            195                 200                 205

Leu His Val Pro Glu Asn Pro Ser Thr Lys Asn Met Met Gly Ala Lys
        210                 215                 220

Glu Ile Ser Leu Met Lys Pro Gly Ser Leu Leu Ile Asn Ala Ser Arg
225                 230                 235                 240

Gly Thr Val Val Asp Ile Pro Ala Leu Cys Asp Ala Leu Ala Ser Lys
                245                 250                 255

His Leu Ala Gly Ala Ala Ile Asp Val Phe Pro Thr Glu Pro Ala Thr
                260                 265                 270

Asn Ser Asp Pro Phe Thr Ser Pro Leu Cys Glu Phe Asp Asn Val Leu
            275                 280                 285

Leu Thr Pro His Ile Gly Gly Ser Thr Gln Glu Ala Gln Glu Asn Ile
        290                 295                 300

Gly Leu Glu Val Ala Gly Lys Leu Ile Lys Tyr Ser Asp Asn Gly Ser
305                 310                 315                 320
```

Thr Leu Ser Ala Val Asn Phe Pro Glu Val Ser Leu Pro Leu His Val
            325                 330                 335

Gly Arg Arg Leu Met His Ile His Glu Asn Arg Pro Gly Val Leu Thr
            340                 345                 350

Ala Leu Asn Lys Ile Phe Ala Glu Gln Gly Val Asn Ile Ala Ala Gln
            355                 360                 365

Tyr Leu Gln Thr Ser Ala Gln Met Gly Tyr Val Val Ile Asp Ile Glu
370                 375                 380

Ala Asp Glu Asp Val Ala Glu Lys Ala Leu Gln Ala Met Lys Ala Ile
385                 390                 395                 400

Pro Gly Thr Ile Arg Ala Arg Leu Leu Tyr
            405                 410

<210> SEQ ID NO 6
<211> LENGTH: 410
<212> TYPE: PRT
<213> ORGANISM: Artificial Sequence
<220> FEATURE:
<223> OTHER INFORMATION: D-3-phosphoglycerate dehydrogenase(G336V,
      G337V), SerA(G336V,G337V)

<400> SEQUENCE: 6

Met Ala Lys Val Ser Leu Glu Lys Asp Lys Ile Lys Phe Leu Leu Val
1               5                   10                  15

Glu Gly Val His Gln Lys Ala Leu Glu Ser Leu Arg Ala Ala Gly Tyr
            20                  25                  30

Thr Asn Ile Glu Phe His Lys Gly Ala Leu Asp Asp Glu Gln Leu Lys
        35                  40                  45

Glu Ser Ile Arg Asp Ala His Phe Ile Gly Leu Arg Ser Arg Thr His
    50                  55                  60

Leu Thr Glu Asp Val Ile Asn Ala Ala Glu Lys Leu Val Ala Ile Gly
65                  70                  75                  80

Cys Phe Cys Ile Gly Thr Asn Gln Val Asp Leu Asp Ala Ala Ala Lys
                85                  90                  95

Arg Gly Ile Pro Val Phe Asn Ala Pro Phe Ser Asn Thr Arg Ser Val
            100                 105                 110

Ala Glu Leu Val Ile Gly Glu Leu Leu Leu Leu Leu Arg Gly Val Pro
        115                 120                 125

Glu Ala Asn Ala Lys Ala His Arg Gly Val Trp Asn Lys Leu Ala Ala
130                 135                 140

Gly Ser Phe Glu Ala Arg Gly Lys Lys Leu Gly Ile Ile Gly Tyr Gly
145                 150                 155                 160

His Ile Gly Thr Gln Leu Gly Ile Leu Ala Glu Ser Leu Gly Met Tyr
                165                 170                 175

Val Tyr Phe Tyr Asp Ile Glu Asn Lys Leu Pro Leu Gly Asn Ala Thr
            180                 185                 190

Gln Val Gln His Leu Ser Asp Leu Leu Asn Met Ser Asp Val Val Ser
        195                 200                 205

Leu His Val Pro Glu Asn Pro Ser Thr Lys Asn Met Met Gly Ala Lys
210                 215                 220

Glu Ile Ser Leu Met Lys Pro Gly Ser Leu Leu Ile Asn Ala Ser Arg
225                 230                 235                 240

Gly Thr Val Val Asp Ile Pro Ala Leu Cys Asp Ala Leu Ala Ser Lys
                245                 250                 255

His Leu Ala Gly Ala Ala Ile Asp Val Phe Pro Thr Glu Pro Ala Thr
            260                 265                 270

```
Asn Ser Asp Pro Phe Thr Ser Pro Leu Cys Glu Phe Asp Asn Val Leu
        275                 280                 285

Leu Thr Pro His Ile Gly Gly Ser Thr Gln Glu Ala Gln Glu Asn Ile
        290                 295                 300

Gly Leu Glu Val Ala Gly Lys Leu Ile Lys Tyr Ser Asp Asn Gly Ser
305                 310                 315                 320

Thr Leu Ser Ala Val Asn Phe Pro Glu Val Ser Leu Pro Leu His Val
                325                 330                 335

Val Arg Arg Leu Met His Ile His Glu Asn Arg Pro Gly Val Leu Thr
                340                 345                 350

Ala Leu Asn Lys Ile Phe Ala Glu Gln Gly Val Asn Ile Ala Ala Gln
        355                 360                 365

Tyr Leu Gln Thr Ser Ala Gln Met Gly Tyr Val Val Ile Asp Ile Glu
        370                 375                 380

Ala Asp Glu Asp Val Ala Glu Lys Ala Leu Gln Ala Met Lys Ala Ile
385                 390                 395                 400

Pro Gly Thr Ile Arg Ala Arg Leu Leu Tyr
                405                 410

<210> SEQ ID NO 7
<211> LENGTH: 410
<212> TYPE: PRT
<213> ORGANISM: Artificial Sequence
<220> FEATURE:
<223> OTHER INFORMATION: D-3-phosphoglycerate dehydrogenase(G336V,
      R338G), SerA(G336V, R338G)

<400> SEQUENCE: 7

Met Ala Lys Val Ser Leu Glu Lys Asp Lys Ile Lys Phe Leu Leu Val
  1               5                  10                  15

Glu Gly Val His Gln Lys Ala Leu Glu Ser Leu Arg Ala Ala Gly Tyr
             20                  25                  30

Thr Asn Ile Glu Phe His Lys Gly Ala Leu Asp Asp Glu Gln Leu Lys
         35                  40                  45

Glu Ser Ile Arg Asp Ala His Phe Ile Gly Leu Arg Ser Arg Thr His
     50                  55                  60

Leu Thr Glu Asp Val Ile Asn Ala Ala Glu Lys Leu Val Ala Ile Gly
 65                  70                  75                  80

Cys Phe Cys Ile Gly Thr Asn Gln Val Asp Leu Asp Ala Ala Ala Lys
                 85                  90                  95

Arg Gly Ile Pro Val Phe Asn Ala Pro Phe Ser Asn Thr Arg Ser Val
            100                 105                 110

Ala Glu Leu Val Ile Gly Glu Leu Leu Leu Leu Leu Arg Gly Val Pro
        115                 120                 125

Glu Ala Asn Ala Lys Ala His Arg Gly Val Trp Asn Lys Leu Ala Ala
    130                 135                 140

Gly Ser Phe Glu Ala Arg Gly Lys Lys Leu Gly Ile Ile Gly Tyr Gly
145                 150                 155                 160

His Ile Gly Thr Gln Leu Gly Ile Leu Ala Glu Ser Leu Gly Met Tyr
                165                 170                 175

Val Tyr Phe Tyr Asp Ile Glu Asn Lys Leu Pro Leu Gly Asn Ala Thr
            180                 185                 190

Gln Val Gln His Leu Ser Asp Leu Leu Asn Met Ser Asp Val Val Ser
        195                 200                 205

Leu His Val Pro Glu Asn Pro Ser Thr Lys Asn Met Met Gly Ala Lys
    210                 215                 220
```

```
Glu Ile Ser Leu Met Lys Pro Gly Ser Leu Leu Ile Asn Ala Ser Arg
225                 230                 235                 240

Gly Thr Val Val Asp Ile Pro Ala Leu Cys Asp Ala Leu Ala Ser Lys
                245                 250                 255

His Leu Ala Gly Ala Ala Ile Asp Val Phe Pro Thr Glu Pro Ala Thr
            260                 265                 270

Asn Ser Asp Pro Phe Thr Ser Pro Leu Cys Glu Phe Asp Asn Val Leu
        275                 280                 285

Leu Thr Pro His Ile Gly Gly Ser Thr Gln Glu Ala Gln Glu Asn Ile
    290                 295                 300

Gly Leu Glu Val Ala Gly Lys Leu Ile Lys Tyr Ser Asp Asn Gly Ser
305                 310                 315                 320

Thr Leu Ser Ala Val Asn Phe Pro Glu Val Ser Leu Pro Leu His Val
                325                 330                 335

Gly Gly Arg Leu Met His Ile His Glu Asn Arg Pro Gly Val Leu Thr
            340                 345                 350

Ala Leu Asn Lys Ile Phe Ala Glu Gln Gly Val Asn Ile Ala Ala Gln
        355                 360                 365

Tyr Leu Gln Thr Ser Ala Gln Met Gly Tyr Val Val Ile Asp Ile Glu
    370                 375                 380

Ala Asp Glu Asp Val Ala Glu Lys Ala Leu Gln Ala Met Lys Ala Ile
385                 390                 395                 400

Pro Gly Thr Ile Arg Ala Arg Leu Leu Tyr
                405                 410

<210> SEQ ID NO 8
<211> LENGTH: 362
<212> TYPE: PRT
<213> ORGANISM: Artificial Sequence
<220> FEATURE:
<223> OTHER INFORMATION: 3-phosphoserine/phosphohydroxythreonine
      aminotransferase, SerC

<400> SEQUENCE: 8

Met Ala Gln Ile Phe Asn Phe Ser Ser Gly Pro Ala Met Leu Pro Ala
1               5                   10                  15

Glu Val Leu Lys Gln Ala Gln Gln Glu Leu Arg Asp Trp Asn Gly Leu
                20                  25                  30

Gly Thr Ser Val Met Glu Val Ser His Arg Gly Lys Glu Phe Ile Gln
            35                  40                  45

Val Ala Glu Glu Ala Glu Lys Asp Phe Arg Asp Leu Leu Asn Val Pro
        50                  55                  60

Ser Asn Tyr Lys Val Leu Phe Cys His Gly Gly Gly Arg Gly Gln Phe
65                  70                  75                  80

Ala Ala Val Pro Leu Asn Ile Leu Gly Asp Lys Thr Thr Ala Asp Tyr
                85                  90                  95

Val Asp Ala Gly Tyr Trp Ala Ala Ser Ala Ile Lys Glu Ala Lys Lys
            100                 105                 110

Tyr Cys Thr Pro Asn Val Phe Asp Ala Lys Val Thr Val Asp Gly Leu
        115                 120                 125

Arg Ala Val Lys Pro Met Arg Glu Trp Gln Leu Ser Asp Asn Ala Ala
    130                 135                 140

Tyr Met His Tyr Cys Pro Asn Glu Thr Ile Asp Gly Ile Ala Ile Asp
145                 150                 155                 160

Glu Thr Pro Asp Phe Gly Ala Asp Val Val Val Ala Ala Asp Phe Ser
                165                 170                 175
```

```
Ser Thr Ile Leu Ser Arg Pro Ile Asp Val Ser Arg Tyr Gly Val Ile
            180                 185                 190

Tyr Ala Gly Ala Gln Lys Asn Ile Gly Pro Ala Gly Leu Thr Ile Val
            195                 200             205

Ile Val Arg Glu Asp Leu Leu Gly Lys Ala Asn Ile Ala Cys Pro Ser
210                 215                 220

Ile Leu Asp Tyr Ser Ile Leu Asn Asp Gly Ser Met Phe Asn Thr
225                 230                 235                 240

Pro Pro Thr Phe Ala Trp Tyr Leu Ser Gly Leu Val Phe Lys Trp Leu
                245                 250                 255

Lys Ala Asn Gly Gly Val Ala Glu Met Asp Lys Ile Asn Gln Gln Lys
            260                 265                 270

Ala Glu Leu Leu Tyr Gly Val Ile Asp Asn Ser Asp Phe Tyr Arg Asn
            275                 280                 285

Asp Val Ala Lys Ala Asn Arg Ser Arg Met Asn Val Pro Phe Gln Leu
290                 295                 300

Ala Asp Ser Ala Leu Asp Lys Leu Phe Leu Glu Glu Ser Phe Ala Ala
305                 310                 315                 320

Gly Leu His Ala Leu Lys Gly His Arg Val Val Gly Gly Met Arg Ala
                325                 330                 335

Ser Ile Tyr Asn Ala Met Pro Leu Glu Gly Val Lys Ala Leu Thr Asp
            340                 345                 350

Phe Met Val Glu Phe Glu Arg Arg His Gly
            355                 360

<210> SEQ ID NO 9
<211> LENGTH: 323
<212> TYPE: PRT
<213> ORGANISM: Mycobacterium smegmatics str. MC2 155
<220> FEATURE:
<221> NAME/KEY: PEPTIDE
<222> LOCATION: (1)..(323)
<223> OTHER INFORMATION: Msm-OPSS

<400> SEQUENCE: 9

Met Thr Arg Tyr Asp Ser Leu Leu Gln Ala Leu Gly Asn Thr Pro Leu
1               5                   10                  15

Val Gly Leu Gln Asn Leu Ser Pro Arg Trp Asp Asp Glu Asp Gly Lys
            20                  25                  30

Pro His Val Arg Leu Trp Ala Lys Leu Glu Asp Arg Asn Pro Thr Gly
        35                  40                  45

Ser Ile Lys Asp Arg Pro Ala Leu Arg Met Ile Glu Gln Ala Glu Arg
    50                  55                  60

Asp Gly Leu Leu Gln Pro Gly Ala Thr Ile Leu Glu Pro Thr Ser Gly
65                  70                  75                  80

Asn Thr Gly Ile Ser Leu Ala Met Ala Ala Leu Leu Lys Gly Tyr Asn
                85                  90                  95

Met Ile Cys Val Met Pro Glu Asn Thr Ser Ile Glu Arg Arg Gln Ile
            100                 105                 110

Leu Glu Leu Tyr Gly Ala Arg Ile Ile Phe Ser Pro Ala Glu Gly Gly
        115                 120                 125

Ser Asn Thr Ala Val Ala Thr Ala Lys Glu Leu Ala Ala Gln Asn Pro
    130                 135                 140

Ser Trp Val Met Leu Tyr Gln Tyr Gly Asn Pro Ala Asn Ser Asp Ala
145                 150                 155                 160

His Tyr Phe Gly Thr Gly Pro Glu Leu Leu Ala Asp Leu Pro Glu Ile
```

```
                     165                 170                 175
Thr His Phe Val Ala Gly Leu Gly Thr Thr Gly Thr Leu Met Gly Thr
                 180                 185                 190

Gly Arg Phe Leu Arg Glu His Val Pro Gly Val Gln Ile Val Ala Ala
            195                 200                 205

Glu Pro Arg Tyr Gly Glu Gly Val Tyr Ala Leu Arg Asn Ile Asp Glu
        210                 215                 220

Gly Phe Ile Pro Glu Leu Tyr Asp Ala Asp Val Leu Thr Thr Arg Phe
225                 230                 235                 240

Ser Val Gly Ser Phe Asp Ala Val Arg Arg Thr Arg Glu Leu Val Thr
                245                 250                 255

Arg Glu Gly Ile Phe Ala Gly Ile Ser Thr Gly Ala Val Leu His Ala
            260                 265                 270

Ala Leu Gly Met Ala Ala Lys Ala Val Lys Ala Gly Glu Arg Ala Asp
        275                 280                 285

Ile Ala Phe Val Val Ala Asp Ala Gly Trp Lys Tyr Leu Ser Thr Gly
290                 295                 300

Ala Tyr Ala Gly Ser Leu Asp Asp Ala Glu Asp Ala Leu Glu Gly Gln
305                 310                 315                 320

Leu Trp Ala

<210> SEQ ID NO 10
<211> LENGTH: 318
<212> TYPE: PRT
<213> ORGANISM: Mycobacterium smegmatics str. MC2 155
<220> FEATURE:
<221> NAME/KEY: PEPTIDE
<222> LOCATION: (1)..(318)
<223> OTHER INFORMATION: Msm-T

<400> SEQUENCE: 10

Met Thr Arg Tyr Asp Ser Leu Leu Gln Ala Leu Gly Asn Thr Pro Leu
1               5                   10                  15

Val Gly Leu Gln Asn Leu Ser Pro Arg Trp Asp Asp Glu Asp Gly Lys
            20                  25                  30

Pro His Val Arg Leu Trp Ala Lys Leu Glu Asp Arg Asn Pro Thr Gly
        35                  40                  45

Ser Ile Lys Asp Arg Pro Ala Leu Arg Met Ile Glu Gln Ala Glu Arg
    50                  55                  60

Asp Gly Leu Leu Gln Pro Gly Ala Thr Ile Leu Glu Pro Thr Ser Gly
65                  70                  75                  80

Asn Thr Gly Ile Ser Leu Ala Met Ala Ala Leu Leu Lys Gly Tyr Asn
                85                  90                  95

Met Ile Cys Val Met Pro Glu Asn Thr Ser Ile Glu Arg Arg Gln Ile
            100                 105                 110

Leu Glu Leu Tyr Gly Ala Arg Ile Ile Phe Ser Pro Ala Glu Gly Gly
        115                 120                 125

Ser Asn Thr Ala Val Ala Thr Ala Lys Glu Leu Ala Ala Gln Asn Pro
    130                 135                 140

Ser Trp Val Met Leu Tyr Gln Tyr Gly Asn Pro Ala Asn Ser Asp Ala
145                 150                 155                 160

His Tyr Phe Gly Thr Gly Pro Glu Leu Leu Ala Asp Leu Pro Glu Ile
                165                 170                 175

Thr His Phe Val Ala Gly Leu Gly Thr Thr Gly Thr Leu Met Gly Thr
            180                 185                 190

Gly Arg Phe Leu Arg Glu His Val Pro Gly Val Gln Ile Val Ala Ala
```

-continued

```
                 195                 200                 205
Glu Pro Arg Tyr Gly Glu Gly Val Tyr Ala Leu Arg Asn Ile Asp Glu
210                 215                 220

Gly Phe Ile Pro Glu Leu Tyr Asp Ala Asp Val Leu Thr Thr Arg Phe
225                 230                 235                 240

Ser Val Gly Ser Phe Asp Ala Val Arg Arg Thr Arg Glu Leu Val Thr
                245                 250                 255

Arg Glu Gly Ile Phe Ala Gly Ile Ser Thr Gly Ala Val Leu His Ala
                260                 265                 270

Ala Leu Gly Met Ala Ala Lys Ala Val Lys Ala Gly Glu Arg Ala Asp
                275                 280                 285

Ile Ala Phe Val Val Ala Asp Ala Gly Trp Lys Tyr Leu Ser Thr Gly
                290                 295                 300

Ala Tyr Ala Gly Ser Leu Asp Asp Ala Glu Asp Ala Leu Glu
305                 310                 315
```

<210> SEQ ID NO 11
<211> LENGTH: 318
<212> TYPE: PRT
<213> ORGANISM: Mycobacterium tuberculosis H37Rv
<220> FEATURE:
<221> NAME/KEY: PEPTIDE
<222> LOCATION: (1)..(318)
<223> OTHER INFORMATION: Mtb-T

<400> SEQUENCE: 11

```
Met Thr Arg Tyr Asp Ser Leu Leu Gln Ala Leu Gly Asn Thr Pro Leu
1               5                   10                  15

Val Gly Leu Gln Arg Leu Ser Pro Arg Trp Asp Asp Gly Arg Asp Gly
                20                  25                  30

Pro His Val Arg Leu Trp Ala Lys Leu Glu Asp Arg Asn Pro Thr Gly
            35                  40                  45

Ser Ile Lys Asp Arg Pro Ala Val Arg Met Ile Glu Gln Ala Glu Ala
        50                  55                  60

Asp Gly Leu Leu Arg Pro Gly Ala Thr Ile Leu Glu Pro Thr Ser Gly
65                  70                  75                  80

Asn Thr Gly Ile Ser Leu Ala Met Ala Ala Arg Leu Lys Gly Tyr Arg
                85                  90                  95

Leu Ile Cys Val Met Pro Glu Asn Thr Ser Val Glu Arg Arg Gln Leu
                100                 105                 110

Leu Glu Leu Tyr Gly Ala Gln Ile Ile Phe Ser Ala Ala Glu Gly Gly
            115                 120                 125

Ser Asn Thr Ala Val Ala Thr Ala Lys Glu Leu Ala Ala Thr Asn Pro
        130                 135                 140

Ser Trp Val Met Leu Tyr Gln Tyr Gly Asn Pro Ala Asn Thr Asp Ser
145                 150                 155                 160

His Tyr Cys Gly Thr Gly Pro Glu Leu Leu Ala Asp Leu Pro Glu Ile
                165                 170                 175

Thr His Phe Val Ala Gly Leu Gly Thr Thr Gly Thr Leu Met Gly Thr
                180                 185                 190

Gly Arg Phe Leu Arg Glu His Val Ala Asn Val Lys Ile Val Ala Ala
            195                 200                 205

Glu Pro Arg Tyr Gly Glu Gly Val Tyr Ala Leu Arg Asn Met Asp Glu
        210                 215                 220

Gly Phe Val Pro Glu Leu Tyr Asp Pro Glu Ile Leu Thr Ala Arg Tyr
225                 230                 235                 240
```

Ser Val Gly Ala Val Asp Ala Val Arg Arg Thr Arg Glu Leu Val His
            245                 250                 255

Thr Glu Gly Ile Phe Ala Gly Ile Ser Thr Gly Ala Val Leu His Ala
            260                 265                 270

Ala Leu Gly Val Gly Ala Gly Leu Ala Ala Gly Glu Arg Ala Asp
            275                 280                 285

Ile Ala Leu Val Val Ala Asp Ala Gly Trp Lys Tyr Leu Ser Thr Gly
            290                 295                 300

Ala Tyr Ala Gly Ser Leu Asp Asp Ala Glu Thr Ala Leu Glu
305                 310                 315

<210> SEQ ID NO 12
<211> LENGTH: 389
<212> TYPE: PRT
<213> ORGANISM: Artificial Sequence
<220> FEATURE:
<223> OTHER INFORMATION: Ape-OPSS

<400> SEQUENCE: 12

Met Ala Leu Ala Asp Ile Ser Gly Tyr Leu Asp Val Leu Asp Ser Val
 1               5                  10                  15

Arg Gly Phe Ser Tyr Leu Glu Asn Ala Arg Glu Val Leu Arg Ser Gly
            20                  25                  30

Glu Ala Arg Cys Leu Gly Asn Pro Arg Ser Glu Pro Glu Tyr Val Lys
        35                  40                  45

Ala Leu Tyr Val Ile Gly Ala Ser Arg Ile Pro Val Gly Asp Gly Cys
    50                  55                  60

Ser His Thr Leu Glu Glu Leu Gly Val Phe Asp Ile Ser Val Pro Gly
65                  70                  75                  80

Glu Met Val Phe Pro Ser Pro Leu Asp Phe Phe Glu Arg Gly Lys Pro
                85                  90                  95

Thr Pro Leu Val Arg Ser Arg Leu Gln Leu Pro Asn Gly Val Arg Val
            100                 105                 110

Trp Leu Lys Leu Glu Trp Tyr Asn Pro Phe Ser Leu Ser Val Lys Asp
        115                 120                 125

Arg Pro Ala Val Glu Ile Ile Ser Arg Leu Ser Arg Arg Val Glu Lys
    130                 135                 140

Gly Ser Leu Val Ala Asp Ala Thr Ser Ser Asn Phe Gly Val Ala Leu
145                 150                 155                 160

Ser Ala Val Ala Arg Leu Tyr Gly Tyr Arg Ala Arg Val Tyr Leu Pro
                165                 170                 175

Gly Ala Ala Glu Glu Phe Gly Lys Leu Leu Pro Arg Leu Leu Gly Ala
            180                 185                 190

Gln Val Ile Val Asp Pro Glu Ala Pro Ser Thr Val His Leu Leu Pro
        195                 200                 205

Arg Val Met Lys Asp Ser Lys Asn Glu Gly Phe Val His Val Asn Gln
    210                 215                 220

Phe Tyr Asn Asp Ala Asn Phe Glu Ala His Met Arg Gly Thr Ala Arg
225                 230                 235                 240

Glu Ile Phe Val Gln Ser Arg Arg Gly Gly Leu Ala Leu Arg Gly Val
                245                 250                 255

Ala Gly Ser Leu Gly Thr Ser Gly His Met Ser Ala Ala Ala Phe Tyr
            260                 265                 270

Leu Gln Ser Val Asp Pro Ser Ile Arg Ala Val Leu Val Gln Pro Ala
        275                 280                 285

Gln Gly Asp Ser Ile Pro Gly Ile Arg Arg Val Glu Thr Gly Met Leu

|     |     |     |     |     |     |     |     |     |     |     |
| --- | --- | --- | --- | --- | --- | --- | --- | --- | --- | --- |
|     |     | 290 |     |     |     | 295 |     |     |     | 300 |

Trp Ile Asn Met Leu Asp Ile Ser Tyr Thr Leu Ala Glu Val Thr Leu
305                 310                 315                 320

Glu Glu Ala Met Glu Ala Val Val Glu Val Ala Arg Ser Asp Gly Leu
            325                 330                 335

Val Ile Gly Pro Ser Gly Gly Ala Val Lys Ala Leu Ala Lys Lys
        340                 345                 350

Ala Ala Glu Gly Asp Leu Glu Pro Gly Asp Tyr Val Val Val Pro
    355                 360                 365

Asp Thr Gly Phe Lys Tyr Leu Ser Leu Val Gln Asn Ala Leu Glu Gly
    370                 375                 380

Ala Gly Asp Ser Val
385

<210> SEQ ID NO 13
<211> LENGTH: 1341
<212> TYPE: DNA
<213> ORGANISM: Corynebacterium glutamicum 13032
<220> FEATURE:
<221> NAME/KEY: gene
<222> LOCATION: (1)..(1341)
<223> OTHER INFORMATION: serB

<400> SEQUENCE: 13

| | |
|---|---|
| atgtcgtgtt ccgcgctcag acatgagaca attgttgccg tgactgaact catccagaat | 60 |
| gaatcccaag aaatcgctga gctggaagcc ggccagcagg ttgcattgcg tgaaggttat | 120 |
| cttcctgcgg tgatcacagt gagcggtaaa gaccgcccag gtgtgactgc cgcgttcttt | 180 |
| agggtcttgt ccgctaatca ggttcaggtc ttggacgttg agcagtcaat gttccgtggc | 240 |
| tttttgaact tggcggcgtt tgtgggtatc gcacctgagc gtgtcgagac cgtcaccaca | 300 |
| ggcctgactg acaccctcaa ggtgcatgga cagtccgtgg tggtgagct gcaggaaact | 360 |
| gtgcagtcgt cccgtcctcg ttcttcccat gttgttgtgg tgttgggtga tccggttgat | 420 |
| gcgttggata tttcccgcat tggtcagacc ctggcggatt acgatgccaa cattgacacc | 480 |
| attcgtggta tttcggatta ccctgtgacc ggcctggagc tgaaggtgac tgtgccggat | 540 |
| gtcagccctg gtggtggtga agcgatgcgt aaggcgcttg ctgctcttac ctctgagctg | 600 |
| aatgtgata ttgcgattga gcgttctggt ttgctgcgtc gttctaagcg tctggtgtgc | 660 |
| ttcgattgtg attccacgtt gatcactggt gaggtcattg agatgctggc ggctcacgcg | 720 |
| ggcaaggaag ctgaagttgc ggcagttact gagcgtgcga tgcgcggtga gctcgatttc | 780 |
| gaggagtctc tgcgtgagcg tgtgaaggcg ttggctggtt tggatgcgtc ggtgatcgat | 840 |
| gaggtcgctg ccgctattga gctgaccccct ggtgcgcgca ccacgatccg tacgctgaac | 900 |
| cgcatgggtt accagaccgc tgttgtttcc ggtggtttca tccaggtgtt ggaaggtttg | 960 |
| gctgaggagt tggagttgga ttatgtccgc gccaacactt tggaaatcgt tgatggcaag | 1020 |
| ctgaccggca acgtcaccgg aaagatcgtt gaccgcgctg cgaaggctga gttcctccgt | 1080 |
| gagttcgctg cggattctgg cctgaagatg taccagactg tcgctgtcgg tgatggcgct | 1140 |
| aatgacatcg atatgctctc cgctgcgggt ctgggtgttg ctttcaacgc gaagcctgcg | 1200 |
| ctgaaggaga ttgcggatac ttccgtgaac cacccattcc tcgacgaggt tttgcacatc | 1260 |
| atgggcattt cccgcgacga gatcgatctg gcggatcagg aagacggcac tttccaccgc | 1320 |
| gttccattga ccaatgccta a | 1341 |

<210> SEQ ID NO 14

<211> LENGTH: 1593
<212> TYPE: DNA
<213> ORGANISM: Artificial Sequence
<220> FEATURE:
<223> OTHER INFORMATION: serA*(E235K)

<400> SEQUENCE: 14

| | |
|---|---|
| atgagccaga atggccgtcc ggtagtcctc atcgccgata agcttgcgca gtccactgtt | 60 |
| gacgcgcttg gagatgcagt agaagtccgt tgggttgacg gacctaaccg cccagaactg | 120 |
| cttgatgcag ttaaggaagc ggacgcactg ctcgtgcgtt ctgctaccac tgtcgatgct | 180 |
| gaagtcatcg ccgctgcccc taacttgaag atcgtcggtc gtgccggcgt gggcttggac | 240 |
| aacgttgaca tccctgctgc cactgaagct ggcgtcatgg ttgctaacgc accgacctct | 300 |
| aatattcact ccgcttgtga gcacgcaatt tctttgctgc tgtctactgc tcgccagatc | 360 |
| cctgctgctg atgcgacgct gcgtgagggc gagtggaagc ggtcttcttt caacggtgtg | 420 |
| gaaattttcg gaaaaactgt cggtatcgtc ggttttggcc acattggtca gttgtttgct | 480 |
| cagcgtcttg ctgcgtttga gaccaccatt gttgcttacg atccttacgc taaccctgct | 540 |
| cgtgcggctc agctgaacgt tgagttggtt gagttggatg agctgatgag ccgttctgac | 600 |
| tttgtcacca ttcaccttcc taagaccaag gaaactgctg gcatgtttga tgcgcagctc | 660 |
| cttgctaagt ccaagaaggg ccagatcatc atcaacgctg ctcgtggtgg ccttgttgat | 720 |
| gagcaggctt tggctgatgc gattgagtcc ggtcacattc gtggcgctgg tttcgatgtg | 780 |
| tactccaccg agccttgcac tgattctcct tgttcaagt tgcctcaggt tgttgtgact | 840 |
| cctcacttgg gtgcttctac tgaagaggct caggatcgtg cgggtactga cgttgctgat | 900 |
| tctgtgctca aggcgctggc tggcgagttc gtggcgatg ctgtgaacgt ttccggtggt | 960 |
| cgcgtgggcg aaaaggttgc tgtgtggatg gatctggctc gcaagcttgg tcttcttgct | 1020 |
| ggcaagcttg tcgacgccgc cccagtctcc attgaggttg aggctcgagg cgagctttct | 1080 |
| tccgagcagg tcgatgcact tggtttgtcc gctgttcgtg gtttgttctc cggaattatc | 1140 |
| gaagagtccg ttactttcgt caacgctcct cgcattgctg aagagcgtgg cctggacatc | 1200 |
| tccgtgaaga ccaactctga gtctgttact caccgttccg tcctgcaggt caaggtcatt | 1260 |
| actggcagcg gcgcgagcgc aactgttgtt ggtgccctga ctggtcttga gcgcgttgag | 1320 |
| aagatcaccc gcatcaatgg ccgtggcctg gatctgcgcg cagagggtct gaacctcttc | 1380 |
| ctgcagtaca ctgacgctcc tggtgcactg gtaccgttg gtaccaagct gggtgctgct | 1440 |
| ggcatcaaca tcgaggctgc tgcgttgact caggctgaga agggtgacgg cgctgtcctg | 1500 |
| atcctgcgtg ttgagtccgc tgtctctgaa gagctggaag ctgaaatcaa cgctgagttg | 1560 |
| ggtgctactt ccttccaggt tgatcttgac taa | 1593 |

<210> SEQ ID NO 15
<211> LENGTH: 1002
<212> TYPE: DNA
<213> ORGANISM: Artificial Sequence
<220> FEATURE:
<223> OTHER INFORMATION: serA*(197 delta)

<400> SEQUENCE: 15

| | |
|---|---|
| atgagccaga atggccgtcc ggtagtcctc atcgccgata agcttgcgca gtccactgtt | 60 |
| gacgcgcttg gagatgcagt agaagtccgt tgggttgacg gacctaaccg cccagaactg | 120 |
| cttgatgcag ttaaggaagc ggacgcactg ctcgtgcgtt ctgctaccac tgtcgatgct | 180 |
| gaagtcatcg ccgctgcccc taacttgaag atcgtcggtc gtgccggcgt gggcttggac | 240 |

-continued

| | |
|---|---|
| aacgttgaca tccctgctgc cactgaagct ggcgtcatgg ttgctaacgc accgacctct | 300 |
| aatattcact ccgcttgtga gcacgcaatt tctttgctgc tgtctactgc tcgccagatc | 360 |
| cctgctgctg atgcgacgct gcgtgagggc gagtggaagc ggtcttcttt caacggtgtg | 420 |
| gaaattttcg gaaaaactgt cggtatcgtc ggttttggcc acattggtca gttgtttgct | 480 |
| cagcgtcttg ctgcgtttga gaccaccatt gttgcttacg atccttacgc taaccctgct | 540 |
| cgtgcggctc agctgaacgt tgagttggtt gagttggatg agctgatgag ccgttctgac | 600 |
| tttgtcacca ttcaccttcc taagaccaag gaaactgctg gcatgtttga tgcgcagctc | 660 |
| cttgctaagt ccaagaaggg ccagatcatc atcaacgctg ctcgtggtgg ccttgttgat | 720 |
| gagcaggctt tggctgatgc gattgagtcc ggtcacattc gtggcgctgg tttcgatgtg | 780 |
| tactccaccg agccttgcac tgattctcct ttgttcaagt tgcctcaggt tgttgtgact | 840 |
| cctcacttgg gtgcttctac tgaagaggct caggatcgtg cgggtactga cgttgctgat | 900 |
| tctgtgctca aggcgctggc tggcgagttc gtggcggatg ctgtgaacgt ttccggtggt | 960 |
| cgcgtgggcg aagaggttgc tgtgtggatg gatctggctt aa | 1002 |

<210> SEQ ID NO 16
<211> LENGTH: 969
<212> TYPE: DNA
<213> ORGANISM: Escherichia coli K12 W3110
<220> FEATURE:
<221> NAME/KEY: gene
<222> LOCATION: (1)..(969)
<223> OTHER INFORMATION: serB

<400> SEQUENCE: 16

| | |
|---|---|
| atgcctaaca ttacctggtg cgacctgcct gaagatgtct ctttatggcc gggtctgcct | 60 |
| cttcattaa gtggtgatga agtgatgcca ctggattacc acgcaggtcg tagcggctgg | 120 |
| ctgctgtatg gtcgtgggct ggataaacaa cgtctgaccc aataccagag caaactgggt | 180 |
| gcggcgatgg tgattgttgc cgcctggtgc gtggaagatt atcaggtgat tcgtctggca | 240 |
| ggttcactca ccgcacgggc tacacgcctg gcccacgaag cgcagctgga tgtcgccccg | 300 |
| ctggggaaaa tcccgcacct gcgcacgccg ggtttgctgg tgatggatat ggactccacc | 360 |
| gccatccaga ttgaatgtat tgatgaaatt gccaaactgg ccggaacggg cgagatggtg | 420 |
| gcggaagtaa ccgaacgggc gatgcgcggc gaactcgatt ttaccgccag cctgcgcagc | 480 |
| cgtgtggcga cgctgaaagg cgctgacgcc aatattctgc aacaggtgcg tgaaaatctg | 540 |
| ccgctgatgc aggcttaac gcaactggtg ctcaagctgg aaacgctggg ctggaaagtg | 600 |
| gcgattgcct ccggcggctt tactttcttt gctgaatacc tgcgcgacaa gctgcgcctg | 660 |
| accgccgtgg tagccaatga actggagatc atggacggta aatttaccgg caatgtgatc | 720 |
| ggcgacatcg tagacgcgca gtacaaagcg aaaactctga ctcgcctcgc gcaggagtat | 780 |
| gaaatcccgc tggcgcagac cgtggcgatt ggcgatggag ccaatgacct gccgatgatc | 840 |
| aaagcggcag gctggggat tgcctaccat gccaagccaa agtgaatga aaaggcggaa | 900 |
| gtcaccatcc gtcacgctga cctgatgggg gtattctgca tcctctcagg cagcctgaat | 960 |
| cagaagtaa | 969 |

<210> SEQ ID NO 17
<211> LENGTH: 1233
<212> TYPE: DNA
<213> ORGANISM: Escherichia coli K12 W3110
<220> FEATURE:
<221> NAME/KEY: gene
<222> LOCATION: (1)..(1233)

<223> OTHER INFORMATION: serA

<400> SEQUENCE: 17

| | | | | | | |
|---|---|---|---|---|---|---|
| atggcaaagg | tatcgctgga | gaaagacaag | attaagtttc | tgctggtaga | aggcgtgcac | 60 |
| caaaaggcgc | tggaaagcct | tcgtgcagct | ggttacacca | acatcgaatt | tcacaaaggc | 120 |
| gcgctggatg | atgaacaatt | aaaagaatcc | atccgcgatg | cccacttcat | cggcctgcga | 180 |
| tcccgtaccc | atctgactga | agacgtgatc | aacgccgcag | aaaaactggt | cgctattggc | 240 |
| tgtttctgta | tcggaacaaa | ccaggttgat | ctggatgcgg | cggcaaagcg | cgggatcccg | 300 |
| gtatttaacg | caccgttctc | aaatacgcgc | tctgttgcgg | agctggtgat | tggcgaactg | 360 |
| ctgctgctat | tgcgcggcgt | gccggaagcc | aatgctaaag | cgcaccgtgg | cgtgtggaac | 420 |
| aaactggcgg | cgggttcttt | tgaagcgcgc | ggcaaaaagc | tgggtatcat | cggctacggt | 480 |
| catattggta | cgcaattggg | cattctggct | gaatcgctgg | gaatgtatgt | ttacttttat | 540 |
| gatattgaaa | ataaactgcc | gctgggcaac | gccactcagg | tacagcatct | ttctgacctg | 600 |
| ctgaatatga | gcgatgtggt | gagtctgcat | gtaccagaga | atccgtccac | caaaaatatg | 660 |
| atgggcgcga | aagaaatttc | actaatgaag | cccggctcgc | tgctgattaa | tgcttcgcgc | 720 |
| ggtactgtgg | tggatattcc | ggcgctgtgt | gatgcgctgg | cgagcaaaca | tctggcgggg | 780 |
| gcggcaatcg | acgtattccc | gacggaaccg | cgaccaata | gcgatccatt | tacctctccg | 840 |
| ctgtgtgaat | tcgacaacgt | ccttctgacg | ccacacattg | gcggttcgac | tcaggaagcg | 900 |
| caggagaata | tcggcctgga | agttgcgggt | aaattgatca | agtattctga | caatggctca | 960 |
| acgctctctg | cggtgaactt | cccggaagtc | tcgctgccac | tgcacggtgg | cgtcgtctg | 1020 |
| atgcacatcc | acgaaaaccg | tccgggcgtg | ctaactgcgc | tgaacaaaat | cttcgccgag | 1080 |
| cagggcgtca | acatcgccgc | gcaatatctg | caaacttccg | cccagatggg | ttatgtggtt | 1140 |
| attgatattg | aagccgacga | agacgttgcc | gaaaaagcgc | tgcaggcaat | gaaagctatt | 1200 |
| ccgggtacca | ttcgcgcccg | tctgctgtac | taa | | | 1233 |

<210> SEQ ID NO 18
<211> LENGTH: 1233
<212> TYPE: DNA
<213> ORGANISM: Artificial Sequence
<220> FEATURE:
<223> OTHER INFORMATION: serA*(G336V)

<400> SEQUENCE: 18

| | | | | | | |
|---|---|---|---|---|---|---|
| atggcaaagg | tatcgctgga | gaaagacaag | attaagtttc | tgctggtaga | aggcgtgcac | 60 |
| caaaaggcgc | tggaaagcct | tcgtgcagct | ggttacacca | acatcgaatt | tcacaaaggc | 120 |
| gcgctggatg | atgaacaatt | aaaagaatcc | atccgcgatg | cccacttcat | cggcctgcga | 180 |
| tcccgtaccc | atctgactga | agacgtgatc | aacgccgcag | aaaaactggt | cgctattggc | 240 |
| tgtttctgta | tcggaacaaa | ccaggttgat | ctggatgcgg | cggcaaagcg | cgggatcccg | 300 |
| gtatttaacg | caccgttctc | aaatacgcgc | tctgttgcgg | agctggtgat | tggcgaactg | 360 |
| ctgctgctat | tgcgcggcgt | gccggaagcc | aatgctaaag | cgcaccgtgg | cgtgtggaac | 420 |
| aaactggcgg | cgggttcttt | tgaagcgcgc | ggcaaaaagc | tgggtatcat | cggctacggt | 480 |
| catattggta | cgcaattggg | cattctggct | gaatcgctgg | gaatgtatgt | ttacttttat | 540 |
| gatattgaaa | ataaactgcc | gctgggcaac | gccactcagg | tacagcatct | ttctgacctg | 600 |
| ctgaatatga | gcgatgtggt | gagtctgcat | gtaccagaga | atccgtccac | caaaaatatg | 660 |
| atgggcgcga | aagaaatttc | actaatgaag | cccggctcgc | tgctgattaa | tgcttcgcgc | 720 |

```
ggtactgtgg tggatattcc ggcgctgtgt gatgcgctgg cgagcaaaca tctggcgggg      780
gcggcaatcg acgtattccc gacggaaccg gcgaccaata gcgatccatt tacctctccg      840
ctgtgtgaat tcgacaacgt ccttctgacg ccacacattg gcggttcgac tcaggaagcg      900
caggagaata tcggcctgga agttgcgggt aaattgatca agtattctga caatggctca      960
acgctctctg cggtgaactt cccggaagtc tcgctgccac tgcacgttgg cgtcgtctg      1020 atgcacatcc acgaaaaccg tccgggcgtg ctaactgcgc tgaacaaaat cttcgccgag     1080
cagggcgtca acatcgccgc gcaatatctg caaacttccg cccagatggg ttatgtggtt     1140
attgatattg aagccgacga agacgttgcc gaaaaagcgc tgcaggcaat gaaagctatt     1200
ccgggtacca ttcgcgcccg tctgctgtac taa                                  1233

<210> SEQ ID NO 19
<211> LENGTH: 1233
<212> TYPE: DNA
<213> ORGANISM: Artificial Sequence
<220> FEATURE:
<223> OTHER INFORMATION: serA*(G336V,G337V)

<400> SEQUENCE: 19
atggcaaagg tatcgctgga gaaagacaag attaagtttc tgctggtaga aggcgtgcac       60
caaaaggcgc tggaaagcct tcgtgcagct ggttacacca acatcgaatt tcacaaaggc      120
gcgctggatg atgaacaatt aaaagaatcc atccgcgatg cccacttcat cggcctgcga      180
tcccgtaccc atctgactga agacgtgatc aacgccgcag aaaaactggt cgctattggc      240
tgtttctgta tcggaacaaa ccaggttgat ctggatgcgg cggcaaagcg cgggatcccg      300
gtatttaacg caccgttctc aaatacgcgc tctgttgcgg agctggtgat tggcgaactg      360
ctgctgctat tgcgcggcgt gccggaagcc aatgctaaag cgcaccgtgg cgtgtggaac      420
aaactggcgg cgggttcttt tgaagcgcgc ggcaaaaagc tgggtatcat cggctacggt      480
catattggta cgcaattggg cattctggct gaatcgctgg gaatgtatgt ttactttat      540 gatattgaaa ataaactgcc gctgggcaac gccactcagg tacagcatct ttctgacctg      600
ctgaatatga gcgatgtggt gagtctgcat gtaccagaga atccgtccac caaaaatatg      660
atgggcgcga agaaatttc actaatgaag cccggctcgc tgctgattaa tgcttcgcgc      720
ggtactgtgg tggatattcc ggcgctgtgt gatgcgctgg cgagcaaaca tctggcgggg      780
gcggcaatcg acgtattccc gacggaaccg gcgaccaata gcgatccatt tacctctccg      840
ctgtgtgaat tcgacaacgt ccttctgacg ccacacattg gcggttcgac tcaggaagcg      900
caggagaata tcggcctgga agttgcgggt aaattgatca agtattctga caatggctca      960
acgctctctg cggtgaactt cccggaagtc tcgctgccac tgcacgttgt gcgtcgtctg     1020
atgcacatcc acgaaaaccg tccgggcgtg ctaactgcgc tgaacaaaat cttcgccgag     1080
cagggcgtca acatcgccgc gcaatatctg caaacttccg cccagatggg ttatgtggtt     1140
attgatattg aagccgacga agacgttgcc gaaaaagcgc tgcaggcaat gaaagctatt     1200
ccgggtacca ttcgcgcccg tctgctgtac taa                                  1233

<210> SEQ ID NO 20
<211> LENGTH: 1233
<212> TYPE: DNA
<213> ORGANISM: Artificial Sequence
<220> FEATURE:
<223> OTHER INFORMATION: serA*(G336V,R338G)

<400> SEQUENCE: 20
```

| | | | |
|---|---|---|---|
| atggcaaagg | tatcgctgga | gaaagacaag attaagtttc tgctggtaga aggcgtgcac | 60 |
| caaaaggcgc | tggaaagcct | tcgtgcagct ggttacacca acatcgaatt tcacaaaggc | 120 |
| gcgctggatg | atgaacaatt | aaaagaatcc atccgcgatg cccacttcat cggcctgcga | 180 |
| tcccgtaccc | atctgactga | agacgtgatc aacgccgcag aaaaactggt cgctattggc | 240 |
| tgtttctgta | tcggaacaaa | ccaggttgat ctggatgcgg cggcaaagcg cgggatcccg | 300 |
| gtatttaacg | caccgttctc | aaatacgcgc tctgttgcgg agctggtgat tggcgaactg | 360 |
| ctgctgctat | tgcgcggcgt | gccggaagcc aatgctaaag cgcaccgtgg cgtgtggaac | 420 |
| aaactggcgg | cgggttcttt | tgaagcgcgc ggcaaaaagc tgggtatcat cggctacggt | 480 |
| catattggta | cgcaattggg | cattctggct gaatcgctgg gaatgtatgt ttactttat | 540 |
| gatattgaaa | ataaactgcc | gctgggcaac gccactcagg tacagcatct ttctgacctg | 600 |
| ctgaatatga | gcgatgtggt | gagtctgcat gtaccagaga atccgtccac caaaaatatg | 660 |
| atgggcgcga | agaaatttc | actaatgaag cccggctcgc tgctgattaa tgcttcgcgc | 720 |
| ggtactgtgg | tggatattcc | ggcgctgtgt gatgcgctgg cgagcaaaca tctggcgggg | 780 |
| gcggcaatcg | acgtattccc | gacggaaccg gcgaccaata gcgatccatt tacctctccg | 840 |
| ctgtgtgaat | tcgacaacgt | ccttctgacg ccacacattg gcggttcgac tcaggaagcg | 900 |
| caggagaata | tcgcctgga | agttgcgggt aaattgatca agtattctga caatggctca | 960 |
| acgctctctg | cggtgaactt | cccggaagtc tcgctgccac tgcacgttgg gggtcgtctg | 1020 |
| atgcacatcc | acgaaaaccg | tccgggcgtg ctaactgcgc tgaacaaaat cttcgccgag | 1080 |
| cagggcgtca | acatcgccgc | gcaatatctg caaacttccg cccagatggg ttatgtggtt | 1140 |
| attgatattg | aagccgacga | agacgttgcc gaaaaagcgc tgcaggcaat gaaagctatt | 1200 |
| ccgggtacca | ttcgcgcccg | tctgctgtac taa | 1233 |

<210> SEQ ID NO 21
<211> LENGTH: 1089
<212> TYPE: DNA
<213> ORGANISM: Escherichia coli K12 W3110
<220> FEATURE:
<221> NAME/KEY: gene
<222> LOCATION: (1)..(1089)
<223> OTHER INFORMATION: serC

<400> SEQUENCE: 21

| | | | |
|---|---|---|---|
| atggctcaaa | tcttcaattt | tagttctggt ccggcaatgc taccggcaga ggtgcttaaa | 60 |
| caggctcaac | aggaactgcg | cgactggaac ggtcttggta cgtcggtgat ggaagtgagt | 120 |
| caccgtggca | aagagttcat | tcaggttgca gaggaagccg agaaggattt tcgcgatctt | 180 |
| cttaatgtcc | cctccaacta | caaggtatta ttctgccatg gcggtggtcg cggtcagttt | 240 |
| gctgcggtac | cgctgaatat | ctcggtgat aaaaccaccg cagattatgt tgatgccggt | 300 |
| tactgggcgg | caagtgccat | taagaagcg aaaaaatact gcacgcctaa tgtctttgac | 360 |
| gccaaagtga | ctgttgatgg | tctgcgcgcg gttaagccaa tgcgtgaatg caactctctc | 420 |
| gataatgctg | cttatatgca | ttattgcccg aatgaaacca tcgatggtat cgccatcgac | 480 |
| gaaacgccag | acttcggcgc | agatgtggtg gtcgccgctg acttctcttc aaccattctt | 540 |
| tcccgtccga | ttgacgtcag | ccgttatggt gtaatttacg ctggcgcgca gaaaaatatc | 600 |
| ggcccggctg | gcctgacaat | cgtcatcgtt cgtgaagatt tgctgggcaa agcgaatatc | 660 |
| gcgtgtccgt | cgattctgga | ttattccatc ctcaacgata acggctccat gtttaacacg | 720 |
| ccgccgacat | ttgcctggta | tctatctggt ctggtcttta aatggctgaa agcgaacggc | 780 |

```
ggtgtagctg aaatggataa aatcaatcag caaaaagcag aactgctata tggggtgatt    840
gataacagcg atttctaccg caatgacgtg gcgaaagcta accgttcgcg gatgaacgtg    900
ccgttccagt tggcggacag tgcgcttgac aaattgttcc ttgaagagtc ttttgctgct    960
ggccttcatg cactgaaagg tcaccgtgtg gtcggcggaa tgcgcgcttc tatttataac    1020
gccatgccgc tggaaggcgt taaagcgctg acagacttca tggttgagtt cgaacgccgt    1080
cacggttaa                                                             1089

<210> SEQ ID NO 22
<211> LENGTH: 26
<212> TYPE: DNA
<213> ORGANISM: Artificial Sequence
<220> FEATURE:
<223> OTHER INFORMATION: primer for deletion cassette of serB

<400> SEQUENCE: 22
gcgatatcat gaccttagaa tggtgg                                          26

<210> SEQ ID NO 23
<211> LENGTH: 23
<212> TYPE: DNA
<213> ORGANISM: Artificial Sequence
<220> FEATURE:
<223> OTHER INFORMATION: primer for deletion cassette of serB

<400> SEQUENCE: 23
gctctagatc acgcatgcct cgc                                             23

<210> SEQ ID NO 24
<211> LENGTH: 30
<212> TYPE: DNA
<213> ORGANISM: Artificial Sequence
<220> FEATURE:
<223> OTHER INFORMATION: primer for deletion cassette of serB

<400> SEQUENCE: 24
gcgatatcat gtcacccctg tgaaaatgac                                      30

<210> SEQ ID NO 25
<211> LENGTH: 29
<212> TYPE: DNA
<213> ORGANISM: Artificial Sequence
<220> FEATURE:
<223> OTHER INFORMATION: primer for deletion cassette of serB

<400> SEQUENCE: 25
gctctagatc agttcgatac ctggggtat                                       29

<210> SEQ ID NO 26
<211> LENGTH: 24
<212> TYPE: DNA
<213> ORGANISM: Artificial Sequence
<220> FEATURE:
<223> OTHER INFORMATION: primer for deletion cassette of serB

<400> SEQUENCE: 26
atcatgttac tggcaggcgc tatc                                            24

<210> SEQ ID NO 27
<211> LENGTH: 29
<212> TYPE: DNA
<213> ORGANISM: Artificial Sequence
<220> FEATURE:
<223> OTHER INFORMATION: primer for deletion cassette of serB
```

```
<400> SEQUENCE: 27
gctctagatt acaaagtgaa agagagacg                                       29

<210> SEQ ID NO 28
<211> LENGTH: 26
<212> TYPE: DNA
<213> ORGANISM: Artificial Sequence
<220> FEATURE:
<223> OTHER INFORMATION: primer for construction of serA*

<400> SEQUENCE: 28
acgatatcat gagccagaat ggccgt                                          26

<210> SEQ ID NO 29
<211> LENGTH: 28
<212> TYPE: DNA
<213> ORGANISM: Artificial Sequence
<220> FEATURE:
<223> OTHER INFORMATION: primer for construction of serA*

<400> SEQUENCE: 29
cgtctagatt agtcaagatc aacctgga                                        28

<210> SEQ ID NO 30
<211> LENGTH: 41
<212> TYPE: DNA
<213> ORGANISM: Artificial Sequence
<220> FEATURE:
<223> OTHER INFORMATION: primer for construction of serA*(E325K)

<400> SEQUENCE: 30
atccatccac acagcaacct tttcgcccac gcgaccaccg g                         41

<210> SEQ ID NO 31
<211> LENGTH: 41
<212> TYPE: DNA
<213> ORGANISM: Artificial Sequence
<220> FEATURE:
<223> OTHER INFORMATION: primer for construction of serA*(E325K)

<400> SEQUENCE: 31
ccggtggtcg cgtgggcgaa aaggttgctg tgtggatgga t                         41

<210> SEQ ID NO 32
<211> LENGTH: 31
<212> TYPE: DNA
<213> ORGANISM: Artificial Sequence
<220> FEATURE:
<223> OTHER INFORMATION: primer for construction of serA* (197 delta)

<400> SEQUENCE: 32
cgtctagatt aagccagatc catccacaca g                                    31

<210> SEQ ID NO 33
<211> LENGTH: 70
<212> TYPE: DNA
<213> ORGANISM: Artificial Sequence
<220> FEATURE:
<223> OTHER INFORMATION: primer for deletion cassette of serB

<400> SEQUENCE: 33
atgcctaaca ttacctggtg cgacctgcct gaagatgtct ctttatggcc gtgtaggctg     60
gagctgcttc                                                            70

<210> SEQ ID NO 34
```

```
<211> LENGTH: 70
<212> TYPE: DNA
<213> ORGANISM: Artificial Sequence
<220> FEATURE:
<223> OTHER INFORMATION: primer for deletion cassette of serB

<400> SEQUENCE: 34
ggatggcggg ccaccaatta cttctgattc aggctgcctg agaggatgca catatgaata        60
tcctccttag                                                               70

<210> SEQ ID NO 35
<211> LENGTH: 27
<212> TYPE: DNA
<213> ORGANISM: Artificial Sequence
<220> FEATURE:
<223> OTHER INFORMATION: primer for amplification of pself-serB to
      construct pBAC-pself-serB

<400> SEQUENCE: 35
cccaagcttc ttccacccctt tgaaaat                                            27

<210> SEQ ID NO 36
<211> LENGTH: 27
<212> TYPE: DNA
<213> ORGANISM: Artificial Sequence
<220> FEATURE:
<223> OTHER INFORMATION: primer for amplification of pself-serB to
      construct pBAC-pself-serB

<400> SEQUENCE: 36
cccaagcttt tacttctgat tcaggct                                             27

<210> SEQ ID NO 37
<211> LENGTH: 19
<212> TYPE: DNA
<213> ORGANISM: Artificial Sequence
<220> FEATURE:
<223> OTHER INFORMATION: primer for amplification of pself-CTG-serB to
      construct pBAC-pself-CTG-serB

<400> SEQUENCE: 37
ggagccttac tgcctaaca                                                      19

<210> SEQ ID NO 38
<211> LENGTH: 19
<212> TYPE: DNA
<213> ORGANISM: Artificial Sequence
<220> FEATURE:
<223> OTHER INFORMATION: primer for amplification of pself-CTG-serB to
      construct pBAC-pself-CTG-serB

<400> SEQUENCE: 38
tgttaggcag taaggctcc                                                      19

<210> SEQ ID NO 39
<211> LENGTH: 20
<212> TYPE: DNA
<213> ORGANISM: Artificial Sequence
<220> FEATURE:
<223> OTHER INFORMATION: primer for construction of serA*

<400> SEQUENCE: 39
agggcgtggt gaccgataat                                                     20

<210> SEQ ID NO 40
<211> LENGTH: 28
<212> TYPE: DNA
```

<210> SEQ ID NO 40
<211> LENGTH: 28
<212> TYPE: DNA
<213> ORGANISM: Artificial Sequence
<220> FEATURE:
<223> OTHER INFORMATION: primer for construction of serA*

<400> SEQUENCE: 40
cctagagctc cattctggct gaatcgct                                28

<210> SEQ ID NO 41
<211> LENGTH: 26
<212> TYPE: DNA
<213> ORGANISM: Artificial Sequence
<220> FEATURE:
<223> OTHER INFORMATION: primer for construction of serA*

<400> SEQUENCE: 41
acggatcccc cctgagactg actgtt                                  26

<210> SEQ ID NO 42
<211> LENGTH: 37
<212> TYPE: DNA
<213> ORGANISM: Artificial Sequence
<220> FEATURE:
<223> OTHER INFORMATION: primer for construction of serA*(G336V)

<400> SEQUENCE: 42
tctcgctgcc actgcacgtt gggcgtcgtc tgatgca                      37

<210> SEQ ID NO 43
<211> LENGTH: 37
<212> TYPE: DNA
<213> ORGANISM: Artificial Sequence
<220> FEATURE:
<223> OTHER INFORMATION: primer for construction of serA*(G336V)

<400> SEQUENCE: 43
tgcatcagac gacgcccaac gtgcagtggc agcgaga                      37

<210> SEQ ID NO 44
<211> LENGTH: 37
<212> TYPE: DNA
<213> ORGANISM: Artificial Sequence
<220> FEATURE:
<223> OTHER INFORMATION: primer for construction of serA*(G336V, G337V)

<400> SEQUENCE: 44
cgctgccact gcacgttgtg cgtcgtctga tgcacat                      37

<210> SEQ ID NO 45
<211> LENGTH: 37
<212> TYPE: DNA
<213> ORGANISM: Artificial Sequence
<220> FEATURE:
<223> OTHER INFORMATION: primer for construction of serA*(G336V, G337V)

<400> SEQUENCE: 45
atgtgcatca gacgacgcac aacgtgcagt ggcagcg                      37

<210> SEQ ID NO 46
<211> LENGTH: 37
<212> TYPE: DNA
<213> ORGANISM: Artificial Sequence
<220> FEATURE:
<223> OTHER INFORMATION: primer for construction of serA*(G336V, R338G)

<400> SEQUENCE: 46
ctgccactgc acgttgtggg tcgtctgatg cacatcc                      37

<210> SEQ ID NO 47
<211> LENGTH: 37
<212> TYPE: DNA
<213> ORGANISM: Artificial Sequence
<220> FEATURE:
<223> OTHER INFORMATION: primer for construction of serA*(G336V, R338G)

<400> SEQUENCE: 47
ggatgtgcat cagacgaccc acaacgtgca gtggcag        37

<210> SEQ ID NO 48
<211> LENGTH: 28
<212> TYPE: DNA
<213> ORGANISM: Artificial Sequence
<220> FEATURE:
<223> OTHER INFORMATION: primer for amplification of serA to construct
      pCL-Prmf-serA

<400> SEQUENCE: 48
gatatcatgg caaaggtatc gctggaga        28

<210> SEQ ID NO 49
<211> LENGTH: 26
<212> TYPE: DNA
<213> ORGANISM: Artificial Sequence
<220> FEATURE:
<223> OTHER INFORMATION: primer for amplification of serA to construct
      pCL-Prmf-serA

<400> SEQUENCE: 49
aagcttttag tacagcagac gggcgc        26

<210> SEQ ID NO 50
<211> LENGTH: 24
<212> TYPE: DNA
<213> ORGANISM: Artificial Sequence
<220> FEATURE:
<223> OTHER INFORMATION: primer for amplification of serA to construct
      pCL-Prmf-serC

<400> SEQUENCE: 50
gatatcatgg ctcaaatctt caat        24

<210> SEQ ID NO 51
<211> LENGTH: 27
<212> TYPE: DNA
<213> ORGANISM: Artificial Sequence
<220> FEATURE:
<223> OTHER INFORMATION: primer for amplification of serA to construct
      pCL-Prmf-serC

<400> SEQUENCE: 51
cccaagcttt taaccgtgac ggcgttc        27

<210> SEQ ID NO 52
<211> LENGTH: 24
<212> TYPE: DNA
<213> ORGANISM: Artificial Sequence
<220> FEATURE:
<223> OTHER INFORMATION: primer for amplification of serA to construct
      pCL-Prmf-serA-(RBS)serC

<400> SEQUENCE: 52
aagcttacgc aacgtggtga gggg        24

<210> SEQ ID NO 53
<211> LENGTH: 29

```
<212> TYPE: DNA
<213> ORGANISM: Artificial Sequence
<220> FEATURE:
<223> OTHER INFORMATION: forward primer for Ape-OPSS

<400> SEQUENCE: 53
gtcatatgat ggctctggct gacatctct                                      29

<210> SEQ ID NO 54
<211> LENGTH: 29
<212> TYPE: DNA
<213> ORGANISM: Artificial Sequence
<220> FEATURE:
<223> OTHER INFORMATION: reverse primer for Ape-OPSS

<400> SEQUENCE: 54
gtaagctttt aaacagagtc accagcacc                                      29

<210> SEQ ID NO 55
<211> LENGTH: 29
<212> TYPE: DNA
<213> ORGANISM: Artificial Sequence
<220> FEATURE:
<223> OTHER INFORMATION: forward primer for Mtb-OPSS

<400> SEQUENCE: 55
gtcatatgat gacacgatac gactcgctg                                      29

<210> SEQ ID NO 56
<211> LENGTH: 29
<212> TYPE: DNA
<213> ORGANISM: Artificial Sequence
<220> FEATURE:
<223> OTHER INFORMATION: reverse primer for Mtb-OPSS

<400> SEQUENCE: 56
gtaagctttc atgcccatag ttgcccttc                                      29

<210> SEQ ID NO 57
<211> LENGTH: 29
<212> TYPE: DNA
<213> ORGANISM: Artificial Sequence
<220> FEATURE:
<223> OTHER INFORMATION: forward primer for Msm-OPSS

<400> SEQUENCE: 57
ataagctttc atgcccatag ctgcccttc                                      29

<210> SEQ ID NO 58
<211> LENGTH: 29
<212> TYPE: DNA
<213> ORGANISM: Artificial Sequence
<220> FEATURE:
<223> OTHER INFORMATION: reverse primer for Msm-OPSS

<400> SEQUENCE: 58
ataagctttc attccagcgc gtcctcggc                                      29

<210> SEQ ID NO 59
<211> LENGTH: 29
<212> TYPE: DNA
<213> ORGANISM: Artificial Sequence
<220> FEATURE:
<223> OTHER INFORMATION: forward primer for Rjo-OPSS

<400> SEQUENCE: 59
gtcatatgat ggcgcggttc gattcgctg                                      29
```

<210> SEQ ID NO 60
<211> LENGTH: 31
<212> TYPE: DNA
<213> ORGANISM: Artificial Sequence
<220> FEATURE:
<223> OTHER INFORMATION: reverse primer for Rjo-OPSS

<400> SEQUENCE: 60
tagcggccgc tcatgcccac aactgcccct c                              31

<210> SEQ ID NO 61
<211> LENGTH: 29
<212> TYPE: DNA
<213> ORGANISM: Artificial Sequence
<220> FEATURE:
<223> OTHER INFORMATION: forward primer for Nfa-OPSS

<400> SEQUENCE: 61
gtcatatgat ggcacgctac gaatcgctg                                 29

<210> SEQ ID NO 62
<211> LENGTH: 28
<212> TYPE: DNA
<213> ORGANISM: Artificial Sequence
<220> FEATURE:
<223> OTHER INFORMATION: reverse primer for Nfa-OPSS

<400> SEQUENCE: 62
gtaagctttc aggcccagag ctggcctt                                  28

<210> SEQ ID NO 63
<211> LENGTH: 29
<212> TYPE: DNA
<213> ORGANISM: Artificial Sequence
<220> FEATURE:
<223> OTHER INFORMATION: forward primer for Mtb-T

<400> SEQUENCE: 63
gtcatatgat gacacgatac gactcgctg                                 29

<210> SEQ ID NO 64
<211> LENGTH: 29
<212> TYPE: DNA
<213> ORGANISM: Artificial Sequence
<220> FEATURE:
<223> OTHER INFORMATION: reverse primer for Mtb-T

<400> SEQUENCE: 64
gtaagctttc attccagagc ggtctcggc                                 29

<210> SEQ ID NO 65
<211> LENGTH: 29
<212> TYPE: DNA
<213> ORGANISM: Artificial Sequence
<220> FEATURE:
<223> OTHER INFORMATION: forward primer of Msm-T

<400> SEQUENCE: 65
gtcatatgat gacgcgctac gactccctg                                 29

<210> SEQ ID NO 66
<211> LENGTH: 29
<212> TYPE: DNA
<213> ORGANISM: Artificial Sequence
<220> FEATURE:
<223> OTHER INFORMATION: reverse primer of Msm-T

```
<400> SEQUENCE: 66
ataagctttc attccagcgc gtcctcggc                                              29

<210> SEQ ID NO 67
<211> LENGTH: 21
<212> TYPE: DNA
<213> ORGANISM: Artificial Sequence
<220> FEATURE:
<223> OTHER INFORMATION: forward primer of pCL-P(CJ1)-Msm-T

<400> SEQUENCE: 67
gatatcgcag cagccatcat c                                                      21

<210> SEQ ID NO 68
<211> LENGTH: 28
<212> TYPE: DNA
<213> ORGANISM: Artificial Sequence
<220> FEATURE:
<223> OTHER INFORMATION: reverse primer of pCL-P(CJ1)-Msm-T

<400> SEQUENCE: 68
cccaagcttt cattccagcg cgtcctcg                                               28
```